(12) United States Patent
Carle et al.

(10) Patent No.: US 11,696,888 B2
(45) Date of Patent: Jul. 11, 2023

(54) TOPICAL COMPOSITIONS AND METHODS

(71) Applicant: MARY KAY INC., Addison, TX (US)

(72) Inventors: Tiffany Carle, Addison, TX (US);
Wanli Zhao, Addison, TX (US);
Barbara Durkee, Addison, TX (US);
Lisha Vanpelt, Addison, TX (US);
Kathlene Cummings, Addison, TX (US)

(73) Assignee: MARY KAY INC., Addison, TX (US)

( * ) Notice: Subject to any disclaimer, the term of this patent is extended or adjusted under 35 U.S.C. 154(b) by 0 days.

(21) Appl. No.: 17/303,288

(22) Filed: May 26, 2021

(65) Prior Publication Data
US 2021/0369596 A1    Dec. 2, 2021

Related U.S. Application Data

(60) Provisional application No. 63/030,784, filed on May 27, 2020.

(51) Int. Cl.
| | | |
|---|---|---|
| *A61K 36/00* | (2006.01) | |
| *A61K 8/9789* | (2017.01) | |
| *A61K 8/64* | (2006.01) | |
| *A61K 8/73* | (2006.01) | |
| *A61Q 19/00* | (2006.01) | |

(52) U.S. Cl.
CPC .............. *A61K 8/9789* (2017.08); *A61K 8/64* (2013.01); *A61K 8/735* (2013.01); *A61Q 19/007* (2013.01)

(58) Field of Classification Search
CPC ....... A61Q 19/08; A61Q 19/007; A61Q 19/00
See application file for complete search history.

(56) References Cited

U.S. PATENT DOCUMENTS

| | | |
|---|---|---|
| 4,885,169 A | 12/1989 | Gazzani |
| 5,362,494 A | 11/1994 | Zysman et al. |
| 5,702,688 A | 12/1997 | Yu et al. |
| 6,342,208 B1 | 1/2002 | Hyldgaard et al. |
| 8,758,805 B2 | 6/2014 | Rabouille |
| 9,415,019 B2 | 8/2016 | Alonso Fernandez et al. |
| 2008/0171030 A1 | 7/2008 | Jochim et al. |
| 2016/0250137 A1 | 9/2016 | Noor et al. |
| 2018/0207134 A1 | 7/2018 | Palladini et al. |

FOREIGN PATENT DOCUMENTS

| | | | | |
|---|---|---|---|---|
| CA | 2269288 | 3/1999 | | |
| CN | 103181862 | 7/2013 | | |
| CN | 104146925 | 11/2014 | | |
| CN | 108434048 | 8/2018 | | |
| CN | 110279627 A | * 9/2019 | ............... | A61K 8/64 |
| CN | 110279646 | 9/2019 | | |
| CN | 110393690 A | * 11/2019 | | |
| CN | 110664685 A | * 1/2020 | ............... | A61K 8/31 |
| EP | 0443043 | 4/1995 | | |
| EP | 0925783 | 6/1999 | | |
| FR | 2734478 | 11/1996 | | |
| IT | MI20061493 | 1/2008 | | |
| JP | 2968034 | 10/1999 | | |
| WO | WO 1999/033439 | 7/1999 | | |
| WO | WO 2019/056725 | 3/2019 | | |
| WO | WO 2019/107849 | 6/2019 | | |

OTHER PUBLICATIONS

"Z.Bigatti Delicate Skin Duo—20% Off Code FAB20" SkinStore.com, Feb. 3, 2012, http://www.skinstore.com/p-7633-zbigatti-delicate-skin-duo.aspx. Accessed Feb. 12, 2014.
International Search Report and Written Opinion issued in Corresponding PCT Application No. PCT/US2021/070607, dated Oct. 25, 2021.

\* cited by examiner

*Primary Examiner* — Qiuwen Mi
(74) *Attorney, Agent, or Firm* — Norton Rose Fulbright US LLP

(57) ABSTRACT

The present invention relates generally to cosmetic compositions and methods that can be used to increase skin hydration, increase adenosine triphosphate (ATP) production in skin, increase antioxidant capacity of skin, reduce glycation of skin, or a combination thereof. In particular, topical application of the compositions to skin increases adenosine triphosphate (ATP) production in skin by at least 10%, increases antioxidant capacity of skin, and/or reduces glycation of skin by at least 50%. In particular, the compositions can include *Chamomilla recutita* (*Matricaria*) flower extract, *Vitis vinifera* (Grape) seed extract, hydrolyzed sodium hyaluronate, Natural Moisturizing Factors (NMF), and optionally carnosine.

10 Claims, No Drawings

TOPICAL COMPOSITIONS AND METHODS

CROSS-REFERENCE TO RELATED APPLICATIONS

This application claims the benefit of priority to U.S. Provisional Patent Application Ser. No. 63/030,784, filed May 27, 2020, hereby incorporated by reference in its entirety.

BACKGROUND OF THE INVENTION

A. Field of the Invention

The present invention relates generally to cosmetic compositions and methods that can be used to increase skin hydration, increase adenosine triphosphate (ATP) production in skin, increase the antioxidant capacity of skin, reduce glycation of skin, or a combination thereof. In particular, the compositions can include *Chamomilla recutita* (*Matricaria*) flower extract, *Vitis vinifera* (Grape) seed extract, hydrolyzed sodium hyaluronate, Natural Moisturizing Factors (NMF), and optionally carnosine.

B. Description of Related Art

Normal healthy skin has a smooth epidermal layer that acts as a strong barrier to water and environmental damage. Skin color and tone is even and unblemished. Natural firming and hydrating elements such as collagen (which provides skin firmness), elastin (which supplies skin elasticity and rebound) and glycosaminoglycans or GAGs (which keep the skin hydrated) are all abundant. However, aging and various other factors can have a negative effect on the health, function and appearance of skin.

Various factors can lead to different stresses on skin, including ageing, chronic exposure to adverse environmental factors, malnutrition, fatigue, stress, changes in seasons, and other extrinsic and intrinsic factors which may damage skin. These stresses can change the visual appearance, physical properties, or physiological functions of skin and tissue in ways that are considered visually undesirable. Notable and obvious changes include dry skin, coarse surface texture, the development of fine lines and wrinkles, loss of elasticity, decreased skin barrier function, loss of color evenness or tone, and mottled pigmentation. Many of these stressors are difficult or impossible to avoid.

Less obvious but measurable changes which occur as skin and tissue ages or endures chronic environmental insult include a general reduction in cellular and tissue vitality, reduction in cell replication rates, reduced cutaneous blood flow, reduced moisture content, accumulated errors in structure and function, alterations in the normal regulation of common biochemical pathways, and a reduction in the skin's and tissue's ability to remodel and repair itself. Many of the alterations in appearance and function of the skin are caused by changes in the outer epidermal layer of the skin, while others are caused by changes in the lower dermis. Regardless of the stimulus for skin damage, when damage occurs, numerous natural and complex biochemical mechanisms are set into motion in attempts to repair the damage.

Aging slows the natural production of collagen, elastin, and GAGs, which results in unwanted changes in skin such as dryness, itchiness, redness, shadows or dark areas, sagging, thinning, or more noticeable fine lines and wrinkles. Aging also slows the natural production of adenosine triphosphate (ATP), a nucleotide known to drive and participate in intracellular processes including repairs. Dermal levels of ATP decline with age and create an energy deficiency, thereby affecting dermal function and skin appearance. Aging and environmental factors, such as UV exposure and reactive oxidants, also trigger a variety of enzymatic and non-enzymatic modifications in skin. One such non-enzymatic process is the reaction of proteins with reducing sugars (glycation or Maillard reaction). Glycation alters the structure and functional properties of proteins, including collagen, elastin, and GAGs, and adversely affects cellular metabolism. The accumulation of glycation products is observed in skin during aging.

Maintaining skin moisture helps overcome some of these changes. However, maintaining moisture of the skin can be difficult. This is especially true for subjects with skin that is more dry than average (dry skin type). Exposure to sun, wind, dry air, chemicals, solvents, washing, cosmetics, or fabrics are some of the many ways that skin can lose moisture. With so many factors compromising the skin's ability to stay hydrated, a moisturizer alone may not always be enough.

Moisturizers are complex mixtures of chemical agents specially designed to make the external layers of the skin (epidermis) softer and more pliable. They increase the skin's hydration (water content) by reducing evaporation. Naturally occurring skin lipids and sterols, as well as artificial or natural oils, humectants, emollients, lubricants, etc., may be part of the composition of commercial skin moisturizers. They usually are available as commercial products for cosmetic and therapeutic uses, but can also be made at home using common pharmacy ingredients. However, moisturizers are not perfect. Some problems associated with moisturizers include unpleasant tactile properties (e.g., heavy, greasy, or sticky feel), instability, skin-irritation, or insufficient moisturizing capabilities. Many attempts have been ineffective, only addressed one or a few of the undesired outcomes, or caused unacceptable side effects themselves, such as skin irritation or an allergic response. Further, not every effective composition will be compatible with every skin or tissue type. Thus, there is a need for new products that are effective at increasing skin hydration, increasing ATP production in skin, increasing antioxidant capacity of skin, reducing glycation of skin, or a combination thereof.

SUMMARY OF THE INVENTION

The inventors have identified a solution to the problems associated with current cosmetic products. The solution resides in a combination of ingredients including *Chamomilla recutita* (*Matricaria*) flower extract, *Vitis vinifera* (Grape) seed extract, hydrolyzed sodium hyaluronate, Natural Moisturizing Factors (NMF), and optionally carnosine. The combination can be used to increase skin hydration, increase ATP production in skin, increase the antioxidant capacity of skin, reduce glycation of skin, or a combination thereof. In particular, topical application of the compositions to skin increases ATP production in skin by at least 5, 10, 15, or 20%. In particular, topical application of the compositions to skin increases antioxidant capacity of skin to at least 5, 10, 15, 20, 25, 30, 35, 40, or 45 $\mu$M Trolox equivalents. In particular, topical application of the compositions to skin reduces glycation of skin by at least 5, 10, 15, 20, 25, 30, 35, 40, 45, 50, 55, 60, 65, 70, 75, 80, 85, 90, or 95%. Additional benefits can include reducing or mitigating unwanted side effects of current cosmetic products. In some aspects, an effective amount of a combination of *Chamomilla recutita* (*Matricaria*) flower extract, *Vitis vinifera* (Grape) seed extract, hydrolyzed sodium hyaluronate, Natural Moisturizing Factors (NMF), and optionally carnosine is combined with an effective amount of glycerin to boost skin moisture content and/or stimulate the skin's own moisturizing factors. In some aspects, an effective amount of a combination of *Chamomilla recutita* (*Matricaria*) flower extract, *Vitis vinifera* (Grape) seed extract, hydrolyzed sodium hyaluronate, Natural Moisturizing Factors (NMF), and optionally carnosine is combined with an effective amount of caprylyl glycol to attract and bind moisture in the air to the skin's outer layers and protect the skin from moisture loss to the environment.

In some aspects, there is disclosed a topical composition that includes any one of, any combination of, or all of *Chamomilla recutita* (*Matricaria*) flower extract, *Vitis vinifera* (Grape) seed extract, hydrolyzed sodium hyaluronate, Natural Moisturizing Factors (NMF), and carnosine. In some instances, the composition includes an effective amount of *Chamomilla recutita* (*Matricaria*) flower extract, *Vitis vinifera* (Grape) seed extract, hydrolyzed sodium hyaluronate, Natural Moisturizing Factors (NMF), and optionally carnosine. In some instances, the composition includes an amount of *Chamomilla recutita* (*Matricaria*) flower extract, *Vitis vinifera* (Grape) seed extract, hydrolyzed sodium hyaluronate, Natural Moisturizing Factors (NMF), and optionally carnosine effective to increase skin hydration, increase ATP production in skin increase the antioxidant capacity of skin, reduce glycation of skin, or a combination thereof. In some instances, the composition includes an effective amount of *Chamomilla recutita* (*Matricaria*) flower extract, *Vitis vinifera* (Grape) seed extract, hydrolyzed sodium hyaluronate, Natural Moisturizing Factors (NMF), and optionally carnosine to increase ATP production in skin by at least 5, 10, 15, or 20%, increase antioxidant capacity of skin to at least 5, 10, 15, 20, 25, 30, 35, 40, or 45 µM Trolox equivalents, and/or reduce glycation of skin by at least 5, 10, 15, 20, 25, 30, 35, 40, 45, 50, 55, 60, 65, 70, 75, 80, 85, 90, or 95% after topical application of the composition to the skin.

In some instances, Natural Moisturizing Factors contain one or more of: an amino acid, a lactam, an alpha-hydroxy acid, and/or a salt thereof. In some instances, the Natural Moisturizing Factors include sodium PCA, sodium lactate, arginine, aspartic acid, PCA, water, *glycine*, alanine, serine, valine, proline, threonine, isoleucine, histidine, and/or phenylalanine. In some instances, the *Chamomilla recutita* (*Matricaria*) flower extract is an aqueous extract. In some instances, the *Vitis vinifera* (Grape) seed extract is an aqueous extract.

The amounts of the ingredients within the composition can vary (e.g., amounts can be as low as 0.000001% to as high as 98% w/w or any range therein). In some aspects, the topical composition includes 0.001 to 1% by weight of *Chamomilla recutita* (*Matricaria*) flower extract, 0.001 to 0.1% by weight of *Vitis vinifera* (Grape) seed extract, 0.001 to 0.1% by weight of hydrolyzed sodium hyaluronate, 0.001 to 1% by weight of Natural Moisturizing Factors, and/or 0.001 to 1% by weight of carnosine. In some aspects, the topical composition includes 0.001 to 1% by weight of *Chamomilla recutita* (*Matricaria*) flower extract. In some aspects, the topical composition include 0.001 to 0.1% by weight of *Vitis vinifera* (Grape) seed extract. In some aspects, the topical composition includes 0.001 to 0.1% by weight of hydrolyzed sodium hyaluronate. In some aspects, the topical composition includes 0.001 to 1% by weight of Natural Moisturizing Factors. In some aspects, the topical composition includes 0.001 to 1% by weight of carnosine.

In some instances, the composition further includes water, glycerin, and/or caprylyl glycol. In some instances, the composition further includes 1 to 95% by weight water; 1 to 15% by weight glycerin; and/or 0.01 to 1% by weight caprylyl glycol.

In some instances, the composition further contains dimethicone, propanediol, and/or betaine. In some instances, the composition includes 0.1 to 10% by weight dimethicone; 0.1 to 10% by weight propanediol; and/or 0.1 to 5% by weight betaine. In some instances, the composition includes an effective amount of one or more of: dimethicone, propanediol, and/or betaine, to increase skin moisture content and/or protect skin from moisture loss to the environment.

In some instances, the composition further includes cetearyl ethylhexanoate, pentylene glycol, dimethicone, cyclopentasiloxane, PEG-12 dimethicone, and/or dimethiconol. In some instances, the composition includes: 1 to 10% by weight cetearyl ethylhexanoate; 1 to 10% by weight pentylene glycol; 0.1 to 10% by weight dimethicone; 0.1 to 5% by weight cyclopentasiloxane; 0.01 to 3% by weight PEG-12 dimethicone; and/or 0.01 to 1% by weight dimethiconol. In some instances, the composition includes an effective amount of one or more of: cetearyl ethylhexanoate, pentylene glycol, dimethicone, cyclopentasiloxane, PEG-12 dimethicone, and/or dimethiconol, to increase skin moisture content and/or protect skin from moisture loss to the environment.

In some instances, the composition further includes 1,2-hexanediol. In some instances, the composition includes 0.001 to 1% by weight 1,2-hexanediol. In some instances, the composition includes an effective amount of 1,2-hexanediol to increase skin moisture content and/or protect skin from moisture loss to the environment.

In some instances, the composition further includes dimethicone, caprylic/capric triglyceride, squalene, butylene glycol, cyclopentasiloxane, *Prunus armeniaca* (Apricot) kernel oil, dipropylene glycol, pyroglutamic acid dimethicone (PCA dimethicone), betaine, and/or hydrogenated lecithin. In some instances, the composition includes: 0.1 to 10% by weight dimethicone; 0.1 to 10% by weight caprylic/capric triglyceride; 0.1 to 10% by weight squalene; 0.1 to 10% by weight butylene glycol; 0.1 to 5% by weight cyclopentasiloxane; 0.1 to 5% by weight *Prunus armeniaca* (Apricot) kernel oil; 0.1 to 5% by weight dipropylene glycol; 0.01 to 3% by weight PCA dimethicone; 0.1 to 3% by weight betaine; and/or 0.1 to 1% by weight hydrogenated lecithin. In some instances, the composition includes an effective amount of one or more of: dimethicone, caprylic/capric triglyceride, squalene, butylene glycol, cyclopentasiloxane, *Prunus armeniaca* (Apricot) kernel oil, dipropylene glycol, pyroglutamic acid dimethicone (PCA dimethicone), betaine, and/or hydrogenated lecithin, to increase skin moisture content and/or protect skin from moisture loss to the environment.

In some aspects, the compositions of the present invention can further include a surfactant, a silicone containing compounds, a UV agent, an oil, and/or other ingredients identified in this specification or those known in the art. The composition can be a lotion, cream, body butter, mask, scrub, cleanser, cream, toner, wash, gel, serum, emulsion (e.g., oil-in-water, water-in-oil, silicone-in-water, water-in-silicone, water-in-oil-in-water, oil-in-water-in-oil, oil-in-water-in-silicone, etc.), solutions (e.g., aqueous or hydro-alcoholic solutions), anhydrous bases (e.g., lipstick or a powder), ointments, milk, paste, aerosol, solid forms, eye jellies, gel serums, gel emulsions, etc. The composition can be formulated for topical skin application at least 1, 2, 3, 4, 5, 6, 7, or more times a day during use. In some aspects of the present invention, compositions can be storage stable or color stable, or both. It is also contemplated that the viscosity of the composition can be selected to achieve a desired result, e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, cps, etc., as measured on a Brookfield Viscometer using a TC spindle at 2.5 rpm at 25° C.).

The compositions, in non-limiting aspects, can have a pH of about 6 to about 9. In some aspects, the pH can be 1, 2, 3, 4, 5, 6, 7, 8, 9, 10, 11, 12, 13, or 14. The compositions can include a triglyceride. Non-limiting examples include small, medium, and large chain triglycerides. In certain aspects, the triglyceride is a medium chain triglyceride (e.g., caprylic capric triglyceride). The compositions can also include preservatives. Non-limiting examples of preservatives include phenoxyethanol, methylparaben, propylparaben, iodopropynyl butylcarbamate, potassium sorbate, sodium benzoate, or any mixture thereof. In some embodiments, the composition is paraben-free.

Compositions of the present invention can have UVA and UVB absorption properties. The compositions can have a sun protection factor (SPF) of 2, 3, 4, 5, 6, 7, 8, 9, 10, 11, 12, 13, 14, 15, 20, 25, 30, 35, 40, 45, 50, 55, 60, or more, or any integer or derivative therein. The compositions can be sunscreen lotions, sprays, creams, toners, serums, cleansers, or masks.

The compositions of the present invention can also include any one of, any combination of, or all of the following additional ingredients: a conditioning agent, a moisturizing agent, a pH adjuster, a structuring agent, inorganic salts, a preservative, a thickening agent, a silicone containing compound, an essential oil, a fragrance, a vitamin, a pharmaceutical ingredient, or an antioxidant, or any combination of such ingredients or mixtures of such ingredients. In certain aspects, the composition can include at least two, three, four, five, six, seven, eight, nine, ten, or more, or all of these additional ingredients identified in the previous sentence. Non-limiting examples of these additional ingredients are identified throughout this specification and are incorporated into this section by reference. The amounts of such ingredients can range from 0.0001% to 99.9% by weight or volume of the composition, or any integer or range in between as disclosed in other sections of this specification, which are incorporated into this paragraph by reference.

Methods of use for the compositions disclosed herein are also disclosed. In some aspects, the compositions disclosed herein are used to increase skin hydration. In some aspects, the compositions disclosed herein are used to increase ATP production in skin. In some aspects, the compositions disclosed herein are used to increase antioxidant capacity of skin. In some aspects, the compositions disclosed herein are used to reduce glycation of skin. In some aspects, the compositions disclosed herein are used to increase ATP production in skin by at least 5, 10, 15, or 20% after topical application to skin. In some aspects, the compositions disclosed herein are used to increase antioxidant capacity of skin to at least 5, 10, 15, 20, 25, 30, 35, 40, or 45 µM Trolox equivalents after topical application to skin. In some aspects, the compositions disclosed herein are used to reduce glycation of skin by at least 5, 10, 15, 20, 25, 30, 35, 40, 45, 50, 55, 60, 65, 70, 75, 80, 85, 90, or 95% after topical application to skin.

It is also contemplated that the compositions disclosed throughout this specification can be used as a leave-on or rinse-off composition. By way of example, a leave-on composition can be one that is topically applied to skin and remains on the skin for a period of time (e.g., at least 5, 6, 7, 8, 9, 10, 20, or 30 minutes, or at least 1, 2, 3, 4, 5, 6, 7, 8, 9, 10, 11, 12, 13, 14, 15, 16, 17, 18, 19, 20, 21, 22, 23 or 24 hours, or overnight or throughout the day). Alternatively, a rinse-off composition can be a product that is intended to be applied to the skin and then removed or rinsed from the skin (e.g., with water) within a period of time such as less than 5, 4, 3, 2, or 1 minute. An example of a rinse off composition can be a skin cleanser, shampoo, conditioner, or soap. An example of a leave-on composition can be a skin moisturizer, sunscreen, mask, overnight cream, or a day cream.

Kits that include the compositions of the present invention are also contemplated. In certain embodiments, the composition is comprised in a container. The container can be a bottle, dispenser, or package. The container can dispense a pre-determined amount of the composition. In certain aspects, the compositions is dispensed in a spray, mist, dollop, or liquid. The container can include indicia on its surface. The indicia can be a word, an abbreviation, a picture, or a symbol.

It is contemplated that any embodiment discussed in this specification can be implemented with respect to any method or composition of the invention, and vice versa. Furthermore, compositions of the invention can be used to achieve methods of the invention.

In the context of the present invention, at least the following 38 aspects are described. Aspect 1 includes a method of increasing skin hydration, increasing ATP production in skin, increasing antioxidant capacity of skin, reducing glycation of skin, or a combination thereof. The method comprises topically applying to the skin a composition comprising an effective amount of *Chamomilla recutita* (*Matricaria*) flower extract, *Vitis vinifera* (Grape) seed extract, hydrolyzed sodium hyaluronate, Natural Moisturizing Factors (NMF), and optionally carnosine, wherein topical application of the composition increases skin hydration, increases ATP production in skin, increases antioxidant capacity of skin, and/or reduces glycation of skin. Aspect 2 depends on Aspect 1, wherein the composition comprises 0.001 to 1% by weight of *Chamomilla recutita* (*Matricaria*) flower extract, 0.001 to 0.1% by weight of *Vitis vinifera* (Grape) seed extract, 0.001 to 0.1% by weight of hydrolyzed sodium hyaluronate, 0.001 to 1% by weight of Natural Moisturizing Factors, and/or 0.001 to 1% by weight of carnosine. Aspect 3 depends on Aspect 1, wherein the composition comprises 0.001 to 1% by weight of *Chamomilla recutita* (*Matricaria*) flower extract, 0.001 to 0.1% by weight of *Vitis vinifera* (Grape) seed extract, 0.001 to 0.1% by weight of hydrolyzed sodium hyaluronate, 0.001 to 1% by weight of Natural Moisturizing Factors, and 0.001 to 1% by weight of carnosine. Aspect 4 depends on Aspect 1, wherein the composition comprises 0.001 to 1% by weight of carnosine. Aspect 5 depends on any of Aspects 1 to 4, wherein Natural Moisturizing Factors comprise one or more of: an amino acid, a lactam, an alpha-hydroxy acid, and/or a salt thereof. Aspect 6 depends on any of Aspects 1 to 5, wherein the composition comprises one or more of a humectant, an emollient, a skin protecting agent, and/or a pH adjuster. Aspect 7 depends on any of Aspects 1 to 6, wherein the composition comprises one or more of water, glycerin, and/or caprylyl glycol. Aspect 8 depends on Aspect 7, wherein the composition comprises 1 to 95% by weight water, 1 to 15% by weight glycerin, and/or 0.01 to 1% by weight caprylyl glycol. Aspect 9 depends on any of Aspects 1 to 8, wherein the composition comprises one or more of dimethicone, propanediol, and/or betaine. Aspect 10 depends on Aspect 9, wherein the composition comprises 0.1 to 10% by weight dimethicone, 0.1 to 10% by weight propanediol, and/or 0.1 to 5% by weight betaine. Aspect 11 depends on any of Aspects 1 to 10, wherein the composition comprises one or more of cetearyl ethylhexanoate, pentylene glycol, dimethicone, cyclopentasiloxane, PEG-12 dimethicone, and/or dimethiconol. Aspect 12 depends on Aspect 11, wherein the composition comprises 1 to 10% by weight cetearyl ethylhexanoate, 1 to 10% by weight pentylene glycol, 0.1 to 10% by weight dimethicone, 0.1 to 5% by weight cyclopentasiloxane, 0.01 to 3% by weight PEG-12 dimethicone, and/or 0.01 to 1% by weight dimethiconol. Aspect 13 depends on any of Aspects 1 to 12, wherein the composition comprises 1,2-hexanediol. Aspect 14 depends on Aspect 13, wherein the composition comprises 0.001 to 1% by weight 1,2-hexanediol. Aspect 15 depends on any of Aspects 1 to 14, wherein the composition comprises one or more of dimethicone, caprylic/capric triglyceride, squalene, butylene glycol, cyclopentasiloxane, *Prunus armeniaca* (Apricot) kernel oil, dipropylene glycol, PCA dimethicone, betaine, and/or hydrogenated lecithin. Aspect 16 depends on Aspect 15, wherein the composition comprises 0.1 to 10% by weight dimethicone, 0.1 to 10% by weight caprylic/capric triglyceride, 0.1 to 10% by weight squalene, 0.1 to 10% by weight butylene glycol, 0.1 to 5% by weight cyclopentasiloxane, 0.1 to 5% by weight *Prunus armeniaca* (Apricot) kernel oil, 0.1 to 5% by weight dipropylene glycol, 0.01 to 3% by weight PCA dimethicone, 0.1 to 3% by weight betaine, and/or 0.1 to 1% by weight hydrogenated lecithin. Aspect 17 depends on any of Aspects 1 to 16, wherein the composition comprises an effective amount of *Chamomilla recutita* (*Matricaria*) flower extract, *Vitis vinifera* (Grape) seed extract, hydrolyzed sodium hyaluronate, Natural Moisturizing Factors (NMF), and/or carnosine to increase ATP production in skin by at least 10% after topical application of the composition to the skin. Aspect 18 depends on any of Aspects 1 to 17, wherein the composition comprises an effective amount of *Chamomilla recutita* (*Matricaria*) (German Chamomile) flower extract, *Vitis vinifera* (Grape) seed extract, hydrolyzed sodium hyaluronate, Natural Moisturizing Factors (NMF), and/or carnosine to increase antioxidant capacity of skin after topical application of the composition to the skin. Aspect 19 depends on any of Aspects 1 to 18, wherein the composition comprises an effective amount of *Chamomilla recutita* (*Matricaria*) (German Chamomile) flower extract, *Vitis vinifera* (Grape) seed extract, hydrolyzed sodium hyaluronate, Natural Moisturizing Factors (NMF), and/or carnosine to reduce glycation of skin by at least 50% after topical application of the composition to the skin. Aspect 20 includes a topical composition comprising an effective amount of a combination of *Chamomilla recutita* (*Matricaria*) flower extract, *Vitis vinifera* (Grape) seed extract, hydrolyzed sodium hyaluronate, Natural Moisturizing Factors (NMF), and optionally carnosine, to increase skin hydration, increase ATP production in skin, increase antioxidant capacity of skin, and/or reduce glycation of skin. Aspect 21 depends on Aspect 20, comprising 0.001 to 1% by weight of *Chamomilla recutita* (*Matricaria*) flower extract, 0.001 to 0.1% by weight of *Vitis vinifera* (Grape) seed extract, 0.001 to 0.1% by weight of hydrolyzed sodium hyaluronate, 0.001 to 1% by weight of Natural Moisturizing Factors, and/or 0.001 to 1% by weight of carnosine. Aspect 22 depends on Aspect 20, comprising 0.001 to 1% by weight of *Chamomilla recutita* (*Matricaria*) flower extract, 0.001 to 0.1% by weight of *Vitis vinifera* (Grape) seed extract, 0.001 to 0.1% by weight of hydrolyzed sodium hyaluronate, 0.001 to 1% by weight of Natural Moisturizing Factors, and 0.001 to 1% by weight of carnosine. Aspect 23 depends on Aspect 20, comprising 0.001 to 1% by weight of carnosine. Aspect 24 depends on any of Aspects 20 to 23, wherein Natural Moisturizing Factors comprise one or more of: an amino acid, a lactam, an alpha-hydroxy acid, and/or a salt thereof. Aspect 25 depends on any of Aspects 20 to 24, comprising one or more of a humectant, an emollient, a skin protecting agent, and/or a pH adjuster. Aspect 26 depends on any of Aspects 20 to 25, comprising one or more of water, glycerin, and/or caprylyl glycol. Aspect 27 depends on Aspect 26, comprising 1 to 95% by weight water; 1 to 15% by weight glycerin; and/or 0.01 to 1% by weight caprylyl glycol. Aspect 28 depends on any of Aspects 20 to 27, comprising one or more of dimethicone, propanediol, and/or betaine. Aspect 29 depends on Aspect 28, comprising 0.1 to 10% by weight dimethicone, 0.1 to 10% by weight propanediol, and/or 0.1 to 5% by weight betaine. Aspect 30 depends on any of Aspects 20 to 29, comprising one or more of cetearyl ethylhexanoate, pentylene glycol, dimethicone, cyclopentasiloxane, PEG-12 dimethicone, and/or dimethiconol. Aspect 31 depends on Aspect 30, comprising 1 to 10% by weight cetearyl ethylhexanoate, 1 to 10% by weight pentylene glycol, 0.1 to 10% by weight dimethicone, 0.1 to 5% by weight cyclopentasiloxane, 0.01 to 3% by weight PEG-12 dimethicone, and/or 0.01 to 1% by weight dimethiconol. Aspect 32 depends on any of Aspects 20 to 31, comprising 1,2-hexanediol. Aspect 33 depends on Aspect 32, comprising 0.001 to 1% by weight 1,2-hexanediol. Aspect 34 depends on any of Aspects 20 to 33, comprising one or more of dimethicone, caprylic/capric triglyceride, squalene, butylene glycol, cyclopentasiloxane, *Prunus armeniaca* (Apricot) kernel oil, dipropylene glycol, PCA dimethicone, betaine, and/or hydrogenated lecithin. Aspect 35 depends on Aspect 34, comprising 0.1 to 10% by weight dimethicone, 0.1 to 10% by weight caprylic/capric triglyceride, 0.1 to 10% by weight squalene, 0.1 to 10% by weight butylene glycol, 0.1 to 5% by weight cyclopentasiloxane, 0.1 to 5% by weight *Prunus armeniaca* (Apricot) kernel oil, 0.1 to 5% by weight dipropylene glycol, 0.01 to 3% by weight PCA dimethicone, 0.1 to 3% by weight betaine, and/or 0.1 to 1% by weight hydrogenated lecithin. Aspect 36 depends on any of Aspects 20 to 35, comprising an effective amount of *Chamomilla recutita* (*Matricaria*) flower extract, *Vitis vinifera* (Grape) seed extract, hydrolyzed sodium hyaluronate, Natural Moisturizing Factors (NMF), and/or carnosine to increase ATP production in skin by at least 10% after topical application of the composition to the skin. Aspect 37 depends on any of Aspects 20 to 35, comprising an effective amount of *Chamomilla recutita* (*Matricaria*) flower extract, *Vitis vinifera* (Grape) seed extract, hydrolyzed sodium hyaluronate, Natural Moisturizing Factors (NMF), and/or carnosine to increase antioxidant capacity of skin after topical application of the composition to the skin. Aspect 38 depends on any of Aspects 20 to 35, comprising an effective amount of *Chamomilla recutita* (*Matricaria*) flower extract, *Vitis vinifera* (Grape) seed extract, hydrolyzed sodium hyaluronate, Natural Moisturizing Factors (NMF), and/or carnosine to reduce glycation of skin by at least 50% after topical application of the composition to the skin.

In some embodiments, compositions of the present invention can be pharmaceutically or cosmetically elegant or can have pleasant tactile properties. "Pharmaceutically elegant," "cosmetically elegant," and/or "pleasant tactile properties" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a serum, a gel, a wash, a body butter, a scrub, a foundation, a night cream, a lipstick, a cleanser, a toner, a sunscreen, a mask, an anti-aging product, a deodorant, an antiperspirant, a perfume, a cologne, etc.

"Topical application" means to apply or spread a composition onto the surface of lips or keratinous tissue. "Topical skin composition" includes compositions suitable for topical application on skin and/or keratinous tissue. Such compositions are typically dermatologically-acceptable in that they do not have undue toxicity, incompatibility, instability, allergic response, and the like, when applied to skin and/or keratinous tissue. Topical skin care compositions of the present invention can have a selected viscosity to avoid significant dripping or pooling after application to skin and/or keratinous tissue.

"Keratinous tissue" includes keratin-containing layers disposed as the outermost protective covering of mammals and includes, but is not limited to, lips, skin, hair, and nails.

The term "about" or "approximately" are defined as being close to as understood by one of ordinary skill in the art. In one non-limiting embodiment the terms are defined to be within 10%, preferably within 5%, more preferably within 1%, and most preferably within 0.5%.

The term "substantially" and its variations are refers to ranges within 10%, within 5%, within 1%, or within 0.5%.

The terms "inhibiting" or "reducing" or any variation of these terms includes any measurable decrease or complete inhibition to achieve a desired result. The terms "promote" or "increase" or any variation of these terms includes any measurable increase, such as a measurable increase of a protein or molecule (e.g., matrix proteins such as fibronectin, laminin, collagen, or elastin or molecules such as hyaluronic acid) to achieve a desired result.

The term "effective," as that term is used in the specification and/or claims, means adequate to accomplish a desired, expected, or intended result.

The use of the word "a" or "an" when used in conjunction with the terms "comprising," "including," "having," or "containing," or any variations of these terms, in the claims and/or the specification may mean "one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. With respect to the phrase "consisting essentially of," a basic and novel property of the compositions and methods of the present invention is the ability to reduce the appearance of fine lines and wrinkles, moisturize skin, promote hydration, strengthen and repair skin, firm and condition skin, improve skin barrier function, reduce skin desquamation, reduce skin roughness, and increase skin lubricity.

Other objects, features, and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

As noted above, the present invention provides a solution to the problems associated with current cosmetic products. The solution is premised on the use of a combination of ingredients to increase skin hydration, increase ATP production in skin, increase the antioxidant capacity of skin, reduce glycation of skin, or a combination thereof. In particular, topical application of the compositions to skin can increase adenosine triphosphate (ATP) production in skin by at least 5, 10, 15, or 20%. In particular, topical application of the compositions to skin can increase antioxidant capacity of skin to at least 5, 10, 15, 20, 25, 30, 35, 40, or 45 µM Trolox equivalents. In particular, topical application of the compositions to skin can reduce glycation of skin by at least 5, 10, 15, 20, 25, 30, 35, 40, 45, 50, 55, 60, 65, 70, 75, 80, 85, 90, or 95%. A combination of *Chamomilla recutita* (*Matricaria*) flower extract, *Vitis vinifera* (Grape) seed extract, hydrolyzed sodium hyaluronate, Natural Moisturizing Factors (NMF), and optionally carnosine can be used to create the topical skin compositions.

The following subsections describe non-limiting aspects of the present invention in further detail.

A particular composition of the present invention is designed to work as a topical composition. The composition relies on a unique combination of any one of, any combination of, or all of *Chamomilla recutita* (*Matricaria*) flower extract, *Vitis vinifera* (Grape) seed extract, hydrolyzed sodium hyaluronate, Natural Moisturizing Factors (NMF), and optionally carnosine. These combinations can be used to create topical skin compositions that increase skin hydration, increase ATP production in skin, increase the antioxidant capacity of skin, reduce glycation of skin, or a combination thereof. Non-limiting examples of such compositions are provided in Tables 3 to 6 of Example 3 below.

Some compositions disclosed herein can be applied to the skin and remain on the skin for a period of time (e.g., at least 1, 2, 3, 4, 5, 10, 20, 30, or 60 minutes or more). After which, the composition, if needed, can be rinsed from the skin or peeled from the skin. Some compositions disclosed herein can be applied to the skin and immediately rinsed from the skin. Some compositions disclosed herein can be applied to the skin and absorbed at least in part by the skin.

These and other non-limiting aspects of the present invention are described in the following sections.

A. Active Ingredients

The present invention is premised on a determination that a combination of one or more of active ingredients— *Chamomilla recutita* (*Matricaria*) flower extract, *Vitis vinifera* (Grape) seed extract, hydrolyzed sodium hyaluronate, Natural Moisturizing Factors (NMF), and optionally carnosine—can be used to create topical skin compositions that increase skin hydration, increase ATP production in skin, increase the antioxidant capacity of skin, reduce glycation of skin, or a combination thereof. In particular, topical application of the compositions to skin can increase adenosine triphosphate (ATP) production in skin by at least 5, 10, 15, or 20%. In particular, topical application of the compositions to skin can increase antioxidant capacity of skin to at least 5, 10, 15, 20, 25, 30, 35, 40, or 45 µM Trolox equivalents. In particular, topical application of the compositions to skin can reduce glycation of skin by at least 5, 10, 15, 20, 25, 30, 35, 40, 45, 50, 55, 60, 65, 70, 75, 80, 85, 90, or 95%. A combination of *Chamomilla recutita* (*Matricaria*) flower extract, *Vitis vinifera* (Grape) seed extract, hydrolyzed sodium hyaluronate, Natural Moisturizing Factors (NMF), and optionally carnosine can be used to create the topical skin compositions.

*Chamomilla recutita* (*Matricaria*) flower extract is a floral extract of the *Chamomilla recutita* plant, commonly known as German chamomile. It is an annual plant of the Asteraceae family, native to southern and eastern Europe. *Chamomilla recutita* (*Matricaria*) extract can be supplied by Alban Muller under the tradename Cosme-Phytami German Chamomile FL. In some embodiments, the extract is provided as an aqueous/alcoholic extract. In some embodiments, the aqueous/alcoholic extract is a water and ethanol extract.

*Vitis vinifera* (Grape) seed extract is an extract of *Vitis vinifera* seed. *Vitis vinifera*, commonly known as the grapevine, is indigenous to southern Europe and western Asia, and is today cultivated worldwide. *Vitis vinifera* (Grape) seed extract can be supplied by Active Concepts. In some embodiments, the extract is provided as an extract in an organic solvent. In some embodiments, the organic solvent is butylene glycol.

Hydrolyzed sodium hyaluronate is an oligomeric, hydrolytically degraded sodium hyaluronate. Hyaluronic acid is an anionic, nonsulfated glycosaminoglycan distributed widely throughout human connective, epithelial, and neural tissues. Hyaluronic acid and hyaluronate salts can retain water and keep skin hydrated. Hydrolyzed sodium hyaluronate can be supplied by Tri-K.

Natural moisturizing factors (NMF) are a collection of naturally occurring compounds that keep the outer layer of skin hydrated. NMF may include various amino acids, lactams, alpha-hydroxy acids, and/or their salts. NMF may be supplied as a blend of amino acids, sodium lactate, and sodium pyroglutamic acid (sodium PCA) by Ajinimoto under the tradename Prodew 500. Prodew 500 includes, sodium PCA, sodium lactate, arginine, aspartic acid, PCA, water, *glycine*, alanine, serine, valine, proline, threonine, isoleucine, histidine, and phenylalanine.

Carnosine (β-alanyl-L-histidine) is a dipeptide molecule, made up of β-alanine and histidine. Carnosine can be naturally found in muscle and brain tissues. Carnosine can be supplied by Symrise under the tradename Dragosine.

This combination of ingredients can be used in different product forms to treat various skin conditions. By way of non-limiting examples, the combination of ingredients can be formulated in an emulsion (e.g., oil in water, water in oil), a gel, a serum, a gel emulsion, a gel serum, a lotion, a mask, a scrub, a wash, a cream, or a body butter.

The extracts described herein can be extracts made through extraction methods known in the art and combinations thereof. Non-limiting examples of extraction methods include the use of liquid-liquid extraction, solid phase extraction, aqueous extraction, ethyl acetate, alcohol, acetone, oil, supercritical carbon dioxide, heat, pressure, pressure drop extraction, ultrasonic extraction, etc. Extracts can be a liquid, solid, dried liquid, re-suspended solid, etc.

B. Amounts of Ingredients

It is contemplated that the compositions of the present invention can include any amount of the ingredients discussed in this specification. The compositions can also include any number of combinations of additional ingredients described throughout this specification (e.g., pigments, or additional cosmetic or pharmaceutical ingredients). The concentrations of the any ingredient within the compositions can vary. In non-limiting embodiments, for example, the compositions can comprise, consisting essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

C. Vehicles

The compositions of the present invention can include or be incorporated into all types of vehicles and carriers. The vehicle or carrier can be a pharmaceutically or dermatologically acceptable vehicle or carrier. Non-limiting examples of vehicles or carriers include water, glycerin, alcohol, oil, a silicon containing compound, a silicone compound, and wax. Variations and other appropriate vehicles will be apparent to the skilled artisan and are appropriate for use in the present invention. In certain aspects, the concentrations and combinations of the compounds, ingredients, and agents can be selected in such a way that the combinations are chemically compatible and do not form complexes which precipitate from the finished product.

D. Structure

The compositions of the present invention can be structured or formulated into a variety of different forms. Non-limiting examples include emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydro-alcoholic), anhydrous bases (such as lipsticks and powders), gels, masks, scrubs, body butters, peels, and ointments. Variations and other structures will be apparent to the skilled artisan and are appropriate for use in the present invention.

E. Additional Ingredients

In addition to the combination of ingredients disclosed by the inventors, the compositions can also include additional ingredients such as cosmetic ingredients and pharmaceutical active ingredients. Non-limiting examples of these additional ingredients are described in the following subsections.

1. Cosmetic Ingredients

The CTFA International Cosmetic Ingredient Dictionary and Handbook (2004 and 2008) describes a wide variety of non-limiting cosmetic ingredients that can be used in the context of the present invention. Examples of these ingredient classes include: fragrance agents (artificial and natural; e.g., gluconic acid, phenoxyethanol, and triethanolamine), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), flavoring agents/aroma agents (e.g., *Stevia rebaudiana* (sweetleaf) extract, and menthol), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as para-aminobenzoic acid ("PABA") and corresponding PABA derivatives, titanium dioxide, zinc oxide, etc.), essential oils, vitamins (e.g., A, B, C, D, E, and K), trace metals (e.g., zinc, calcium and selenium), anti-irritants (e.g., steroids and non-steroidal anti-inflammatories), botanical extracts (e.g., *Aloe vera*, chamomile, cucumber extract, *Ginkgo biloba*, ginseng, and rosemary), anti-microbial agents, antioxidants (e.g., BHT and tocopherol), chelating agents (e.g., di sodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, methyl gluceth-20, saccharide isomerate, and mannitol), exfoliants, waterproofing agents (e.g., magnesium/aluminum hydroxide stearate), skin conditioning agents (e.g., *aloe* extracts, allantoin, bisabolol, ceramides, dimethicone, hyaluronic acid, biosaccharide gum-1, ethylhexylglycerin, pentylene glycol, hydrogenated polydecene, octyldodecyl oleate, gluconolactone, calcium gluconate, cyclohexasiloxane, and dipotassium glycyrrhizate). Non-limiting examples of some of these ingredients are provided in the following subsections.

a. UV Absorption and/or Reflecting Agents

UV absorption and/or reflecting agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate (octinoxate), isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloyl trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidene camphor, and isopentyl 4-methoxycinnamate. Non-limiting examples of physical sunblocks include, kaolin, talc, petrolatum and metal oxides (e.g., titanium dioxide and zinc oxide).

b. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrrolidone carboxylic acid, potassium PCA, propylene glycol, saccharide isomerate, sodium glucuronate, sodium PCA, sorbitol, sucrose, trehalose, urea, and xylitol.

Other examples include acetylated lanolin, acetylated lanolin alcohol, alanine, algae extract, *Aloe barbadensis*, *Aloe barbadensis* extract, *Aloe barbadensis* gel, *Althea officinalis* extract, apricot (*Prunus armeniaca*) kernel oil, arginine, arginine aspartate, *Arnica montana* extract, aspartic acid, avocado (*Persea gratissima*) oil, barrier sphingolipids, butyl alcohol, beeswax, behenyl alcohol, beta-sitosterol, birch (*Betula alba*) bark extract, borage (*Borago officinalis*) extract, butcherbroom (*Ruscus aculeatus*) extract, butylene glycol, *Calendula officinalis* extract, *Calendula officinalis* oil, candelilla (*Euphorbia cerifera*) wax, canola oil, caprylic/capric triglyceride, cardamom (*Elettaria cardamomum*) oil, carnauba (*Copernicia cerifera*)

wax, carrot (*Daucus carota sativa*) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, *Eucalyptus globulus* oil, evening primrose (*Oenothera biennis*) oil, fatty acids, *Geranium maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, *glycine*, glycol stearate, glycol stearate SE, glycosaminoglycans, *Vitis vinifera* (Grape) seed oil, hazel (*Corylus americana*) nut oil, hazel (*Corylus avellana*) nut oil, hexylene glycol, hyaluronic acid, hybrid safflower (*Carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*Citrus medica limonum*) oil, linoleic acid, linolenic acid, *Macadamia ternifolia* nut oil, maltitol, *matricaria* (*Chamomilla recutita*) oil, methyl glucose sesquistearate, methylsilanol PCA, mineral oil, mink oil, *mortierella* oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*Citrus aurantium dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG-40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (*Mentha piperita*) oil, petrolatum, phospholipids, plankton extract, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*Oryza sativa*) bran oil, RNA, rosemary (*Rosmarinus officinalis*) oil, rose oil, safflower (*Carthamus tinctorius*) oil, sage (*Salvia officinalis*) oil, sandalwood (*Santalum album*) oil, serine, serum protein, sesame (*Sesamum indicum*) oil, shea butter (*Butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang ylang (*Cananga odorata*) oil.

c. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfate, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

d. Structuring Agents

In other non-limiting aspects, the compositions of the present invention can include a structuring agent. Structuring agent, in certain aspects, assist in providing rheological characteristics to the composition to contribute to the composition's stability. In other aspects, structuring agents can also function as an emulsifier or surfactant. Non-limiting examples of structuring agents include sodium cocoyl glutamate, hydroxypropyl cyclodextrin, stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

e. Emulsifiers

In certain aspects of the present invention, the compositions do not include an emulsifier. In other aspects, however, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (see U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, cetearyl glucoside, cetearyl alcohol, C12-13 pareth-3, PPG-2 methyl glucose ether distearate, PPG-5-ceteth-20, bis-PEG/PPG-20/20 dimethicone, ceteth-10, polysorbate 80, cetyl phosphate, potassium cetyl phosphate, diethanolamine cetyl phosphate, polysorbate 60, glyceryl stearate, PEG-100 stearate, arachidyl alcohol, arachidyl glucoside, and mixtures thereof.

f. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, cyclohexasiloxane, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

g. Exfoliating Agent

Exfoliating agents include ingredients that remove dead skin cells on the skin's outer surface. These agents may act through mechanical, chemical, and/or other means. Non-limiting examples of mechanical exfoliating agents include abrasives such as pumice, silica, cloth, paper, shells, beads, solid crystals, solid polymers, etc. Non-limiting examples of chemical exfoliating agents include acids and enzyme exfoliants. Acids that can be used as exfoliating agents include, but are not limited to, glycolic acid, lactic acid, citric acid, alpha hydroxy acids, beta hydroxy acids, etc. Other exfoliating agents known to those of skill in the art are also contemplated as being useful within the context of the present invention.

h. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, *macadamia* nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, *eucalyptus* oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

i. Thickening Agents

Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene, trihydroxystearin, ammonium acryloyldimethyltaurate/VP copolymer, or a mixture of them.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., CARBOPOL™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a C10-C30 straight chain or branched chain alkyl group through an ether linkage. Typically these polymers are ethers of C10-C30 straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboxymethyl dextran, sodium carrageenan, tragacanth gum, xanthan gum, and mixtures thereof.

j. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal or combinations thereof.

2. Pharmaceutical Ingredients

Pharmaceutical active agents are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antiviral s, antimicrobials, anti-cancer actives, scabicides, pediculicides, antineoplastics, antiperspirants, antipruritics, antipsoriatic agents, anti seborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

F. Kits

Kits are also contemplated as being used in certain aspects of the present invention. For instance, compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit, and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Materials Used

The active ingredients in Table 1 were used to obtain the in vitro data noted below.

TABLE 1

| Ingredient |
| --- |
| *Chamomilla recutita* (*Matricaria*) flower extract can be supplied by Alban Muller under the tradename Cosme-Phytamis German Chamomile FL (5% by weight of *Chamomilla recutita* (*Matricaria*) flower extract) |
| *Vitis vinifera* (Grape) seed extract can be supplied by Active Concepts (20% by weight of *Vitis vinifera* (Grape) seed extract) |
| Hydrolyzed sodium hyaluronate can be supplied by Tri-K |
| Carnosine can be supplied by Symrise under the tradename Dragosine (100% by weight of carnosine). |
| Natural moisturizing factors (NMF) can be supplied by Ajinimoto under the tradename Prodew 500 |

Example 2

In-Vitro Efficacy of Ingredients

It has been determined that *Chamomilla recutita* (*Matricaria*) flower extract, *Vitis vinifera* (Grape) seed extract, hydrolyzed sodium hyaluronate, Natural Moisturizing Factors (NMF), and optionally carnosine can increase skin hydration, increase ATP production in skin, increase the antioxidant capacity of skin, and/or reduce glycation of skin. A summary of results is found in Table 2, and the methods used to determine the properties of the ingredients are provided below.

TABLE 2

| Ingredient | Assay | Activity |
| --- | --- | --- |
| *Vitis vinifera* (Grape) seed extract 0.02 wt. % or 0.1 wt. % | ATP Luminescence (0.02 wt. %) | +20% |
| | ORAC (0.02 wt. %) | 45 µM Trolox Equivalents |
| | ORAC (0.1 wt. %) | 50 µM Trolox Equivalents |
| *Chamomilla recutita* (*Matricaria*) flower extract 0.025 wt. % | Ribose/BSA Glycation | −95% |
| Carnosine 0.1 wt. % | Ribose/BSA Glycation | −38% |

ATP Assay: *Vitis vinifera* (Grape) seed extract has been shown to stimulate production of adenosine triphosphate (ATP). *Vitis vinifera* (Grape) seed extract can be supplied by Active Concepts. Quantitative detection of ATP in human dermal fibroblasts was performed with a firefly luciferase luminescence kit (e.g., Cayman Chemical, ATP Detection Assay Kit—Luminescence #700410) to assess the effects of *Vitis vinifera* (Grape) seed extract on the level of ATP in skin. Briefly, human dermal fibroblasts were seeded onto white 96 well plates for 24 hours, then treated with *Vitis vinifera* (Grape) seed extract for 4 hours. Following incubation, cells were lysed then assayed for ATP levels. The luminescent ATP assay protocol involves lysis of the cell sample, addition of ATP detection assay buffer, luciferase enzyme, and luciferin, and measurement of the emitted light using a tube or microplate-based luminometer. Percent (%) stimulation of ATP production=(ATP levels of treated−ATP levels of untreated control)/ATP levels of untreated control)×100%). Therefore, a positive (+) indicates stimulation of ATP production. The treatment of human dermal fibroblasts with 0.02% by weight *Vitis vinifera* (Grape) seed extract achieved % stimulation of ATP production=+20%.

ORAC Assay: *Vitis vinifera* (Grape) seed extract has been shown to exhibit antioxidant activity. *Vitis vinifera* (Grape) seed extract can be supplied by Active Concepts. Oxygen Radical Absorption (or Absorbance) Capacity (ORAC) of *Vitis vinifera* (Grape) seed extract was assayed by measuring its antioxidant activity. Antioxidant activity indicates a capability to reduce oxidizing agents (oxidants). This assay quantified the degree and length of time it takes for *Vitis vinifera* (Grape) seed extract to inhibit the action of an oxidizing agent. The ORAC value of *Vitis vinifera* (Grape) seed extract was determined by methods known to those of ordinary skill in the art (see U.S. Publication Nos. 2004/0109905 and 2005/0163880; and commercially available kits such as Zen-Bio ORAC Anti-oxidant Assay kit (#AOX-2)). The Zen-Bio ORAC Anti-oxidant Assay kit measured the loss of fluorescein fluorescence over time due to the peroxyl-radical formation by the breakdown of AAPH (2,2'-axobis-2-methyl propanimidamide, dihydrochloride). Trolox, a water soluble vitamin E analog, served as positive control for *Vitis vinifera* (Grape) seed extract's inhibition of fluorescein decay in a dose dependent manner. The ORAC value for 0.02% by weight *Vitis vinifera* (Grape) seed extract was determined to be equivalent to 45 µM Trolox. The ORAC value for 0.1% by weight *Vitis vinifera* (Grape) seed extract was determined to be equivalent to 50 µM Trolox.

Glycation Assay: *Chamomilla recutita* (*Matricaria*) flower extract and carnosine were found to have significant effects on inhibiting glycation. *Chamomilla recutita* (*Matricaria*) flower extract can be supplied by Alban Muller under the tradename Cosme-Phytamis German Chamomile FL. Carnosine can be supplied by Symrise under the tradename Dragosine. A ribose/bovine serum albumin (BSA) assay was used to measure the ability of *Chamomilla recutita* (*Matricaria*) flower extract and carnosine to inhibit glycation of BSA, a homologue to human serum albumin, by D-ribose. D-ribose is a pentose occurring in every cell type and is a component of such important molecules as riboflavin, adenine nucleotides and ribonucleic acids. Ribose has the ability to react with proteins to produce glycated derivatives.

The following assay protocol was used: 0.2M stock solution of ribose was diluted to 0.02 M in phosphate buffer; 20× stock solution of test ingredient was diluted to 2× in 0.02 M ribose; 1M stock solution of AMG was diluted to 0.1M in 0.02 M ribose; 100 µl of 10% BSA solution was added into all wells; 100 µl of 0.02 M ribose was added into control wells (ribose/BSA positive control wells); 100 µl of 0.1M AMG (in 0.02 M ribose) was added into positive control wells; 100 µl of test ingredients (in 0.02 M ribose) was added into test wells; the plate was sealed and incubated at 42° C. for 24 hrs; the fluorescence at 360/460 ex/em was read on a fluorometer. Percent (%) inhibition of glycation=(glycation levels of treated-glycation levels of untreated control)/glycation levels of untreated control)×100%). Therefore, a negative (−) indicates inhibition of glycation. Treatment of BSA with 0.5% by weight *Chamomilla recutita* (*Matricaria*) flower extract demonstrated % inhibition of glycation=−95%. Treatment of BSA with 0.1% by weight Carnosine demonstrated % inhibition of glycation=−20%.

It has been determined that different formulations that include *Chamomilla recutita* (*Matricaria*) flower extract, *Vitis vinifera* (Grape) seed extract, hydrolyzed sodium hyaluronate, Natural Moisturizing Factors (NMF), and optionally carnosine can increase skin hydration. The results are found in Table 3, and the methods used to analyze the effectiveness of the formulations are provided below.

TABLE 3

Hydration Assay Results

Increase in Hydration at Various Time Points

| Formulation | Immediate | 8 hours | 12 hours |
|---|---|---|---|
| Cream | 63% | 27% | 24% |
| Lotion | 44% | 16% | 13% |
| Serum | 71% | 34% | 31% |
| Toner | 34% | 21% | 20% |

Skin Moisture/Hydration Assay: Cream, lotion, serum, and toner formulations that include *Chamomilla recutita* (*Matricaria*) flower extract, *Vitis vinifera* (Grape) seed extract, hydrolyzed sodium hyaluronate, Natural Moisturizing Factors (NMF), and optionally carnosine were found to have significant effects on skin hydration. Skin moisture/hydration benefits were measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit was calibrated according to instrument instructions for each testing day. A notation of temperature and relative humidity was made for each testing day. Subjects (n=28) were evaluated as follows: prior to measurement they can equilibrate in a room with defined humidity (e.g., 30-50%) and temperature (e.g., 68-72° C.). Three separate impedance readings were taken on each side of the face, recorded, and averaged. The T5 setting were used on the impedance meter which averages the impedance values of every five seconds application to the face. Changes in hydration as evidenced by measured conductivity changes, and compared to untreated controls are reported in Table 3. All formulations provided significant (p<0.05) hydration through 12 hours of wear.

Example 3

Exemplary Formulations

Formulations having the ingredients disclosed herein were prepared as topical skin compositions. In some instances, the topical skin compositions can be prepared as an emulsion, serum, gel, gel emulsion, or cream.

Table 4 shows an example of a topical skin composition prepared as a serum.

TABLE 4^

| Ingredient | % Concentration (by weight) |
|---|---|
| Water | 82 |
| Glycerin | 8 |
| Dimethicone | 4 |
| Propanediol | 3 |

TABLE 4^-continued

| Ingredient | % Concentration (by weight) |
|---|---|
| Betaine | 1 |
| Phenoxyethanol | 0.5 |
| Ammonium acryloyldimethyltaurate/VP copolymer | 0.4 |
| Polysorbate 20 | 0.3 |
| Acrylates/C10-C30 alkyl acrylate crosspolymer | 0.3 |
| Caprylyl glycol | 0.1 |
| Carnosine | 0.1 |
| Disodium EDTA | 0.1 |
| NMF* | 0.1 |
| *Chamomilla recutita* (*Matricaria*) flower extract | 0.05 |
| *Vitis vinifera* (Grape) seed extract | 0.02 |
| Hydrolyzed sodium hyaluronate | 0.01 |
| Excipients** | q.s. |

^Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition or ingredients that provide benefits to skin.
*NMF may include a blend of sodium PCA, sodium lactate, arginine, aspartic acid, PCA, glycine, alanine, serine, valine, isoleucine, proline, threonine, and/or histidine.
**Excipients can be added, for example, to modify the rheological properties of the composition. Alternatively, the amount of water can be varied so long as the amount of water in the composition is at least 40% w/w, and preferably between 60 to 90% w/w.

Table 5 shows an example of a topical skin composition prepared as a cream.

TABLE 5^

| Ingredient | % Concentration (by weight) |
|---|---|
| Water | 70 |
| Glycerin | 11 |
| Cetearyl ethylhexanoate | 5 |
| Pentylene glycol | 4 |
| Dimethicone | 3 |
| Silica | 2 |
| Cyclopentasiloxane | 2 |
| Ammonium acryloyldimethyltaurate/VP copolymer | 2 |
| Phenoxyethanol | 0.9 |
| PEG-12 dimethicone | 0.7 |
| Caprylyl glycol | 0.3 |
| Chlorphenesin | 0.2 |
| Carnosine (optional) | 0.1 |
| Dimethiconol | 0.1 |
| NMF* | 0.2 |
| *Chamomilla recutita* (*Matricaria*) flower extract | 0.03 |
| *Vitis vinifera* (Grape) seed extract | 0.02 |
| Hydrolyzed sodium hyaluronate | 0.01 |
| Excipients** | q.s. |

^Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition or ingredients that provide benefits to skin.
*NMF may include a blend of sodium PCA, sodium lactate, arginine, aspartic acid, PCA, glycine, alanine, serine, valine, isoleucine, proline, threonine, and/or histidine.
**Excipients can be added, for example, to modify the rheological properties of the composition. Alternatively, the amount of water can be varied so long as the amount of water in the composition is at least 40% w/w, and preferably between 60 to 80% w/w.

Table 6 shows an example of a topical skin composition prepared as a toner.

TABLE 6^

| Ingredient | % Concentration (by weight) |
|---|---|
| Water | 92 |
| Glycerin | 7 |
| PEG-40 hydrogenated castor oil | 0.4 |
| Caprylyl glycol | 0.3 |
| Hydroxyacetophenone | 0.3 |
| 1,2-Hexanediol | 0.2 |

TABLE 6ˆ-continued

| Ingredient | % Concentration (by weight) |
|---|---|
| Polysorbate 20 | 0.2 |
| Carbomer | 0.2 |
| Carnosine (optional) | 0.1 |
| NMF* | 0.1 |
| Chamomilla recutita (Matricaria) flower extract | 0.03 |
| Hydrolyzed sodium hyaluronate | 0.01 |
| Vitis vinifera (Grape) seed extract | 0.02 |
| Excipients** | q.s. |

ˆFormulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition or ingredients that provide benefits to skin.
*NMF may include a blend of sodium PCA, sodium lactate, arginine, aspartic acid, PCA, glycine, alanine, serine, valine, isoleucine, proline, threonine, and/or histidine.
**Excipients can be added, for example, to modify the rheological properties of the composition. Alternatively, the amount of water can be varied so long as the amount of water in the composition is at least 40% w/w, and preferably between 70 to 95% w/w.

Table 7 shows an example of a topical skin composition prepared as a lotion.

TABLE 7ˆ

| Ingredient | % Concentration (by weight) |
|---|---|
| Water | 76 |
| Dimethicone | 3 |
| Glycerin | 3 |
| Caprylic/Capric triglyceride | 3 |
| Squalane | 3 |
| Butylene glycol | 2 |
| Cyclopentasiloxane | 2 |
| Prunus armeniaca (Apricot) kernel oil | 1 |
| Dipropylene glycol | 1 |
| Sodium polyacrylate | 0.8 |
| PCA dimethicone | 0.7 |
| Silica | 0.7 |
| Betaine | 0.5 |
| Phenoxyethanol | 0.5 |
| Hydroxyacetophenone | 0.3 |
| Dimethicone crosspolymer | 0.2 |
| Hydrogenated lecithin | 0.2 |
| Caprylyl glycol | 0.1 |
| Carnosine (optional) | 0.1 |
| NMF* | 0.1 |
| Vitis vinifera (Grape) seed extract | 0.04 |
| Chamomilla recutita (Matricaria) flower extract | 0.03 |
| Hydrolyzed sodium hyaluronate | 0.01 |
| Excipients** | q.s. |

ˆFormulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition or ingredients that provide benefits to skin.
*NMF may include a blend of sodium PCA, sodium lactate, arginine, aspartic acid, PCA, glycine, alanine, serine, valine, isoleucine, proline, threonine, and/or histidine.
**Excipients can be added, for example, to modify the rheological properties of the composition. Alternatively, the amount of water can be varied so long as the amount of water in the composition is at least 40% w/w, and preferably between 60 to 85% w/w.

Table 8 shows an example of a topical skin composition prepared as a cleanser.

TABLE 8ˆ

| Ingredient | % Concentration (by weight) |
|---|---|
| Water | 75 |
| Sodium C14-C16 olefin sulfonate | 9 |
| Glycerin | 3.6 |
| Disodium cocoamphodiacetate | 2.8 |
| Cocamidopropyl betaine | 2.4 |
| Cocamide monoethanolamine | 2 |
| Sodium methyl cocoyl taurate | 1.2 |
| Benzyl alcohol | 0.8 |
| Glycol stearate | 0.8 |

TABLE 8ˆ-continued

| Ingredient | % Concentration (by weight) |
|---|---|
| PEG-80 sorbitan laurate | 0.6 |
| Sodium chloride | 0.6 |
| Polycarylate crosspolymer-6 | 0.4 |
| Salicylic acid | 0.1 |
| Disodium EDTA | 0.1 |
| Citric acid | 0.1 |
| NMF* | 0.05 |
| Chamomilla recutita (Matricaria) flower extract | 0.03 |
| Sorbic acid | 0.03 |
| Vitis vinifera (Grape) seed extract | 0.02 |
| Polyquaternium-7 | 0.02 |
| Hydrolyzed sodium hyaluronate | 0.01 |
| Excipients** | q.s. |

ˆFormulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition or ingredients that provide benefits to skin.
*NMF may include a blend of sodium PCA, sodium lactate, arginine, aspartic acid, PCA, glycine, alanine, serine, valine, isoleucine, proline, threonine, and/or histidine.
**Excipients can be added, for example, to modify the rheological properties of the composition. Alternatively, the amount of water can be varied so long as the amount of water in the composition is at least 40% w/w, and preferably between 60 to 85% w/w.

Table 9 shows an alternative example of a topical skin composition prepared as a cleanser.

TABLE 9ˆ

| Ingredient | % Concentration (by weight) |
|---|---|
| Water | 72 |
| Cetearyl alcohol | 4.3 |
| Glycerin | 4 |
| Cocamidopropyl betaine | 3.1 |
| Sodium stearoyl glutamate | 2.1 |
| PPG-2 hydroxyethyl coco/isostearamide | 2 |
| Propanediol | 2 |
| Sodium cocoyl glutamate | 2 |
| Acrylates copolymer | 1.7 |
| Sodium methyl cocoyl taurate | 1.5 |
| Hydrolyzed corn starch | 1.5 |
| Magnesium aluminum silicate | 1 |
| Coco-glucoside | 0.7 |
| Potassium hydroxide | 0.6 |
| Sodium chloride | 0.6 |
| Disodium EDTA | 0.15 |
| Citric acid | 0.1 |
| NMF* | 0.05 |
| Chamomilla recutita (Matricaria) flower extract | 0.03 |
| Vitis vinifera (Grape) seed extract | 0.02 |
| Magnesium nitrate | 0.01 |
| Hydrolyzed sodium hyaluronate | 0.01 |
| Excipients** | q.s. |

ˆFormulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition or ingredients that provide benefits to skin.
*NMF may include a blend of sodium PCA, sodium lactate, arginine, aspartic acid, PCA, glycine, alanine, serine, valine, isoleucine, proline, threonine, and/or histidine.
**Excipients can be added, for example, to modify the rheological properties of the composition. Alternatively, the amount of water can be varied so long as the amount of water in the composition is at least 40% w/w, and preferably between 60 to 85% w/w.

Table 10 shows an example of a topical skin composition prepared as a mask.

TABLE 10ˆ

| Ingredient | % Concentration (by weight) |
|---|---|
| Water | 59.6 |
| Isocetyl stearate | 5 |
| Titanium dioxide | 5 |
| Glycerin | 4.5 |
| Magnesium aluminum silicate | 4.5 |

TABLE 10^-continued

| Ingredient | % Concentration (by weight) |
|---|---|
| Kaolin | 4 |
| Stearic acid | 4 |
| Paraffin | 3 |
| Petrolatum | 2.5 |
| Triethanolamine | 2 |
| *Citrus aurantifolia* (Lime) peel powder | 1.5 |
| Cetyl alcohol | 1.5 |
| Phenoxyethanol | 0.6 |
| Bentonite | 0.5 |
| Betaine | 0.5 |
| *Prunus armeniaca* (apricot) seed powder | 0.5 |
| Tea-lauryl sulfate | 0.3 |
| Xanthan gum | 0.2 |
| Dipotassium glycyrrhizate | 0.1 |
| Disodium EDTA | 0.1 |
| NMF* | 0.05 |
| *Chamomilla recutita* (*Matricaria*) flower extract | 0.03 |
| *Vitis vinifera* (Grape) seed extract | 0.02 |
| Hydrolyzed sodium hyaluronate | 0.01 |
| Excipients** | q.s. |

^Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition or ingredients that provide benefits to skin.
*NMF may include a blend of sodium PCA, sodium lactate, arginine, aspartic acid, PCA, glycine, alanine, serine, valine, isoleucine, proline, threonine, and/or histidine.
**Excipients can be added, for example, to modify the rheological properties of the composition. Alternatively, the amount of water can be varied so long as the amount of water in the composition is at least 40% w/w, and preferably between 60 to 85% w/w.

Example 4

Additional Assays

Assays that can be used to determine the efficacy of any one of the ingredients or any combination of ingredients or compositions having said combination of ingredients disclosed throughout the specification and claims can be determined by methods known to those of ordinary skill in the art. The following are non-limiting assays that can be used in the context of the present invention. It should be recognized that other testing procedures can be used, including, for example, objective and subjective procedures.

Antioxidant (AO) Assay: An in vitro bioassay that measures the total anti-oxidant capacity of any one of the ingredients, combination of ingredients, or compositions having said combinations disclosed in the specification. The assay relies on the ability of antioxidants in the sample to inhibit the oxidation of ABTS® (2,2'-azino-di-[3-ethylbenzthiazoline sulphonate]) to ABTS®-+ by metmyoglobin. The antioxidant system of living organisms includes enzymes such as superoxide dismutase, catalase, and glutathione peroxidase; macromolecules such as albumin, ceruloplasmin, and ferritin; and an array of small molecules, including ascorbic acid, α-tocopherol, β-carotene, reduced glutathione, uric acid, and bilirubin. The sum of endogenous and food-derived antioxidants represents the total antioxidant activity of the extracellular fluid. Cooperation of all the different antioxidants provides greater protection against attack by reactive oxygen or nitrogen radicals, than any single compound alone. Thus, the overall antioxidant capacity may give more relevant biological information compared to that obtained by the measurement of individual components, as it considers the cumulative effect of all antioxidants present in plasma and body fluids. The capacity of the antioxidants in the sample to prevent ABTS oxidation is compared with that of Trolox, a water-soluble tocopherol analogue, and is quantified as molar Trolox equivalents. Anti-Oxidant capacity kit #709001 from Cayman Chemical (Ann Arbor, Mich. USA) can be used as an in vitro bioassay to measure the total anti-oxidant capacity of each of any one of the active ingredients, combination of ingredients, or compositions having said combinations disclosed in the specification. The protocol can be followed according to manufacturer recommendations.

Production of Hyaluronic Acid: Changes in the production of hyaluronic acid (HA) in human dermal fibroblasts due to each of the active ingredients, any one of the combination of ingredients, or compositions having said combinations disclosed in the specification can be measured. HA is a polysaccharide involved in stabilization of the structure of the matrix and is involved in providing turgor pressure to tissue and cells. As one non-limiting example, HA production in treated and non-treated adult human dermal fibroblasts (HDFa) cells can be determined using the Hyaluronan DuoSet ELISA kit from R&D Systems (DY3614). In this assay, for production of samples, subconfluent HDFa cells from Cascade Biologics (C-13-5C) are incubated at 37° C. and 10% $CO_2$ in starvation medium (0.15% fetal bovine serum and 1% Penicillin Streptomycin solution in Dulbecco's Modified Eagle Medium) for 72 hours prior to treatment. The cells are then incubated with fresh starvation medium with either test compound, positive control (phorbol 12-myristate 13-acetate from Sigma-Aldrich (P1585) and platelet derived growth factor from Sigma-Aldrich (P3201)), or no additive for 24 hours. Media is then collected and frozen at −80° C. until use in the ELISA assay.

Briefly, the ELISA assay employs a quantitative sandwich enzyme immunoassay technique whereby a capture antibody specific for HA can be pre-coated onto a microplate. Standards and media from treated and untreated cells are pipetted into the microplate wells to enable any HA present to be bound by the immobilized antibody. After washing away any unbound substances, an enzyme-linked detection antibody specific for HA is added to the wells. Following a wash to remove any unbound antibody-enzyme reagent, a substrate solution is added to the wells to allow color development in proportion to the amount of HA bound in the initial step. The color development is stopped at a specific time and the intensity of the color at 450 nm can be measured using a microplate reader.

Laminin and Fibronectin Stimulation Assay: Laminin and fibronectin are major proteins in the dermal-epidermal junction (DEJ) (also referred to as the basement membrane). The DEJ is located between the dermis and the epidermis interlocks forming fingerlike projections called rete ridges. The cells of the epidermis receive their nutrients from the blood vessels in the dermis. The rete ridges increase the surface area of the epidermis that is exposed to these blood vessels and the needed nutrients. The DEJ provides adhesion of the two tissue compartments and governs the structural integrity of the skin. Laminin and fibronectin are two structural glycoproteins located in the DEJ. Considered the glue that holds the cells together, laminin and fibronectin are secreted by dermal fibroblasts to help facilitate intra- and intercellular adhesion of the epidermal calls to the DEJ.

Laminin and fibronectin secretion can be monitored by quantifying laminin and fibronectin in cell supernatants of cultured human fibroblasts treated for 3 days with culture medium with or without 1.0% final concentration of each of the active ingredients, any one of the combination of ingredients, or compositions having said combinations disclosed in the specification. Following incubation, laminin and fibronectin content was measured using immunofluorescent antibodies directed against each protein in an enzyme linked immuno-sorbant assay (ELISA).

Production of Occludin: Changes in the production of occludin in keratinocytes due to each of the active ingredients, any one of the combination of ingredients, or compositions having said combinations disclosed in the specification can be measured. Occludin is a protein critical to the formulation of tight junctions and the skin's moisture barrier function. A non-limiting example of how occludin production in treated and non-treated keratinocytes can be determined is by the use of a bioassay that analyzes occludin concentration in keratinocyte cell lysates. The bioassay can be performed using PROTEINSIMPLE® SIMON™ western blotting protocol. For the samples, adult human epidermal keratinocytes (HEKa) from Life Technologies (C-005-5C) can be grown at 37° C. and 5% CO2 for 24 hours in EPILIFE™ growth media with calcium from Life Technologies (M-EP-500-CA) supplemented with Keratinocyte Growth Supplement (HKGS) from Life Technologies (S-101-5). HEKa are then incubated in growth medium with test compound/extract, no compound/extract for negative control, or with 1 mM $CaCl_2$ for positive control for 24 to 48 hours. The HEKa are then washed, collected, and stored on ice or colder until lysed on ice using a lysis buffer and sonication. The protein concentrations of the samples can be determined and used to normalize the samples. The lysates are stored at −80° C. until use in the bioassay.

The PROTEINSIMPLE® SIMON™ western blotting bioassay assay employs a quantitative western blotting immunoassay technique using an antibody specific for occludin to quantitatively detect occludin in each of the active ingredients, any one of the combination of ingredients, or compositions having said combinations disclosed in the specification. Cell samples are lysed and normalized for protein concentration. Normalized samples and molecular weight standards are then loaded and ran on a denatured protein separation gel using capillary electrophoresis. The proteins in the gel are then immobilized and immunoprobed using a primary antibody specific for occludin. The immobilized proteins are immunoprobed with an enzyme-linked detection antibody that binds the primary antibody. A chemiluminescent substrate solution is then added to the immobilized proteins to allow chemiluminescent development in proportion to the amount of occludin bound in the immobilization. The chemiluminescent development can be stopped at a specific time and the intensity of the chemiluminescent signal can be measured and compared to positive and negative controls.

Keratinocyte Monolayer Permeability: Changes in the permeability of a keratinocyte monolayer due to each of the active ingredients, any one of the combination of ingredients, or compositions having said combinations disclosed in the specification can be measured. Keratinocyte monolayer permeability is a measure of skin barrier integrity. Keratinocyte monolayer permeability in treated and non-treated keratinocytes can be determined using, as a non-limiting example, the In Vitro Vascular Permeability assay by Millipore (ECM642). This assay analyzes endothelial cell adsorption, transport, and permeability. Briefly, adult human epidermal keratinocytes from Life Technologies (C-005-5C) can be seeded onto a porous collagen-coated membrane within a collection well. The keratinocytes are then incubated for 24 hours at 37° C. and 5% $CO_2$ in Epilife growth media with calcium from Life Technologies (M-EP-500-CA) supplemented with Keratinocyte Growth Supplement (HKGS) from Life Technologies (S-101-5). This incubation time allows the cells to form a monolayer and occlude the membrane pores. The media is then replaced with fresh media with (test sample) or without (non-treated control) test compounds/extracts and the keratinocytes are incubated for an additional 48 hours at 37° C. and 5% $CO_2$. To determine permeability of the keratinocyte monolayer after incubation with/without the test compound/extract, the media is replaced with fresh media containing a high molecular weight Fluorescein isothiocyanate (FITC)-Dextran and the keratinocytes are incubated for 4 hours at 37° C. and 5% $CO_2$. During the 4 hours incubation, FITC can pass through the keratinocytes monolayer and porous membrane into the collection well at a rate proportional to the monolayer's permeability. After the 4 hour incubation, cell viability and the content of FITC in the collection wells can be determined. For the FITC content, the media in the collection well is collected and fluorescence of the media determined at 480 nm (Em) when excited at 520 nm. Percent permeability and percent change in comparison to the non-treated controls can be determined by the following equations: Percent Permeability=((Mean Ex/Em of test sample)/Mean Ex/Em untreated control)*100; Percent Change=Percent Permeability of test sample−Percent Permeability of untreated control.

Tumor Necrosis Factor Alpha (TNF-α) Assay: The prototype ligand of the TNF superfamily, TNF-α, is a pleiotropic cytokine that plays a central role in inflammation. Increase in its expression is associated with an up regulation in pro-inflammatory activity. This bioassay can be used to analyze the effect of any one of the active ingredients, combination of ingredients, or compositions having said combinations disclosed in the specification on the production of TNF-α by human epidermal keratinocytes. The endpoint of this assay can be a spectrophotometric measurement that reflects the presence of TNF-α and cellular viability. The assay employs the quantitative sandwich enzyme immunoassay technique whereby a monoclonal antibody specific for TNF-α has been pre-coated onto a microplate. Standards and samples can be pipetted into the wells and any TNF-α present is bound by the immobilized antibody. After washing away any unbound substances, an enzyme-linked polyclonal antibody specific for TNF-α can be added to the wells. Following a wash to remove any unbound antibody-enzyme reagent, a substrate solution can be added to the wells and color developed in proportion to the amount of TNF-α bound in the initial step using a microplate reader for detection at 450 nm. The color development can be stopped and the intensity of the color can be measured. Subconfluent normal human adult keratinocytes (Cascade Biologics) cultivated in EPILIFE™ standard growth medium (Cascade Biologics) at 37° C. in 5% $CO_2$, can be treated with phorbol 12-myristate 13-acetate (PMA, 10 ng/ml, Sigma Chemical, #P1585-1MG) and any one of the active ingredients, combination of ingredients, or compositions having said combinations disclosed in the specification for 6 hours. PMA has been shown to cause a dramatic increase in TNF-α secretion which peaks at 6 hours after treatment. Following incubation, cell culture medium can be collected and the amount of TNF-α secretion quantified using a sandwich enzyme linked immuno-sorbant assay (ELISA) from R&D Systems (#DTA00C).

Mushroom tyrosinase activity assay: In mammalian cells, tyrosinase catalyzes two steps in the multi-step biosynthesis of melanin pigments from tyrosine (and from the polymerization of dopachrome). Tyrosinase is localized in melanocytes and produces melanin (aromatic quinone compounds) that imparts color to skin, hair, and eyes. Purified mushroom tyrosinase (Sigma) can be incubated with its substrate L-Dopa (Fisher) in the presence or absence of each of the active ingredients, any one of the combination of ingredients, or compositions having said combinations disclosed in the specification. Pigment formation can be evaluated by colorimetric plate reading at 490 nm. The percent inhibition of mushroom tyrosinase activity can be calculated compared to non-treated controls to determine the ability of each of the active ingredients, any one of the combination of ingredients, or compositions having said combinations disclosed in the specification to inhibit the activity of purified enzyme. Test extract inhibition was compared with that of kojic acid (Sigma).

Matrix Metalloproteinase 3 and 9 Enzyme Activity (MMP3; MMP9) Assay: An in vitro matrix metalloprotease (MMP) inhibition assay. MMPs are extracellular proteases that play a role in many normal and disease states by virtue of their broad substrate specificity. MMP3 substrates include collagens, fibronectins, and laminin; while MMP9 substrates include collagen VII, fibronectins and laminin. Using Colorimetric Drug Discovery kits from BioMol International for MMP3 (AK-400) and MMP-9 (AK-410), this assay is designed to measure protease activity of MMPs using a thiopeptide as a chromogenic substrate (Ac-PLG42-mercapto-4-methyl-pentanoylRG-OC2H5)5,6. The MMP cleavage site peptide bond is replaced by a thioester bond in the thiopeptide. Hydrolysis of this bond by an MMP produces a sulfhydryl group, which reacts with DTNB [5,5'-dithiobis (2-nitrobenzoic acid), Ellman's reagent] to form 2-nitro-5-thiobenzoic acid, which can be detected by its absorbance at 412 nm ($\varepsilon$=13,600 M-lcm-1 at pH 6.0 and above 7). The active ingredients, any one of the combination of ingredients, or compositions having said combinations disclosed in the specification can be assayed.

Matrix Metalloproteinase 1 Enzyme Activity (MMP1) Assay: An in vitro matrix metalloprotease (MMP) inhibition assay. MMPs are extracellular proteases that play a role in many normal and disease states by virtue of their broad substrate specificity. MMP1 substrates include collagen IV. The Molecular Probes Enz/Chek Gelatinase/Collagenase Assay kit (#E12055) utilizes a fluorogenic gelatin substrate to detect MMP1 protease activity. Upon proteolytic cleavage, bright green fluorescence is revealed and may be monitored using a fluorescent microplate reader to measure enzymatic activity.

The Enz/Chek Gelatinase/Collagenase Assay kit (#E12055) from Invitrogen is designed as an in vitro assay to measure MMP1 enzymatic activity. The active ingredients, any one of the combination of ingredients, or compositions having said combinations disclosed in the specification can be assayed. The assay relies upon the ability of purified MMP1 enzyme to degrade a fluorogenic gelatin substrate. Once the substrate is specifically cleaved by MMP1 bright green fluorescence is revealed and may be monitored using a fluorescent microplate reader. Test materials are incubated in the presence or absence of the purified enzyme and substrate to determine their protease inhibitor capacity.

Cyclooxygenase (COX) Assay: An in vitro cyclooxygenase-1 and -2 (COX-1, -2) inhibition assay. COX is a bifunctional enzyme exhibiting both cyclooxygenase and peroxidase activities. The cyclooxygenase activity converts arachidonic acid to a hydroperoxy endoperoxide (Prostaglandin G2; PGG2) and the peroxidase component reduces the endoperoxide (Prostaglandin H2; PGH2) to the corresponding alcohol, the precursor of prostaglandins, thromboxanes, and prostacyclins. This COX Inhibitor screening assay measures the peroxidase component of cyclooxygenases. The peroxidase activity is assayed colorimetrically by monitoring the appearance of oxidized N,N,N',N'-tetramethyl-p-phenylenediamine (TMPD). This inhibitor screening assay includes both COX-1 and COX-2 enzymes in order to screen isozyme-specific inhibitors. The Colormetric COX (ovine) Inhibitor screening assay (#760111, Cayman Chemical) can be used to analyze the effects of each of the active ingredients, any one of the combination of ingredients, or compositions having said combinations disclosed in the specification on the activity of purified cyclooxygnase enzyme (COX-1 or COX-2). According to manufacturer instructions, purified enzyme, heme and test extracts can be mixed in assay buffer and incubated with shaking for 15 min at room temperature. Following incubation, arachidonic acid and colorimetric substrate can be added to initiate the reaction. Color progression can be evaluated by colorimetric plate reading at 590 nm. The percent inhibition of COX-1 or COX-2 activity can be calculated compared to non-treated controls to determine the ability of test extracts to inhibit the activity of purified enzyme.

Lipoxygenase (LO) Assay: An in vitro lipoxygenase (LO) inhibition assay. LOs are non-heme iron-containing dioxygenases that catalyze the addition of molecular oxygen to fatty acids. Linoleate and arachidonate are the main substrates for LOs in plants and animals. Arachadonic acid may then be converted to hydroxyeicosotrienenoic (HETE) acid derivatives, that are subsequently converted to leukotrienes, potent inflammatory mediators. This assay provides an accurate and convenient method for screening lipoxygenase inhibitors by measuring the hydroperoxides generated from the incubation of a lipoxygenase (5-, 12-, or 15-LO) with arachidonic acid. The Colorimetric LO Inhibitor screening kit (#760700, Cayman Chemical) can be used to determine the ability of each of the active ingredients, any one of the combination of ingredients, or compositions having said combinations disclosed in the specification to inhibit enzyme activity. Purified 15-lipoxygenase and test ingredients can be mixed in assay buffer and incubated with shaking for 10 min at room temperature. Following incubation, arachidonic acid can be added to initiate the reaction and the mixtures can be incubated for an additional 10 min at room temperature. Colorimetric substrate can be added to terminate catalysis and color progression can be evaluated by fluorescence plate reading at 490 nm. The percent inhibition of lipoxyganse activity can be calculated compared to non-treated controls to determine the ability of each of the active ingredients, any one of the combination of ingredients, or compositions having said combinations disclosed in the specification to inhibit the activity of purified enzyme.

Elastase Assay: ENZCHEK® Elastase Assay (Kit #E-12056) from Molecular Probes (Eugene, Oreg. USA) can be used as an in vitro enzyme inhibition assay for measuring inhibition of elastase activity for each of the active ingredients, any one of the combination of ingredients, or compositions having said combinations disclosed in the specification. The EnzChek kit contains soluble bovine neck ligament elastin that can be labeled with dye such that the conjugate's fluorescence can be quenched. The non-fluorescent substrate can be digested by elastase or other proteases to yield highly fluorescent fragments. The resulting increase in fluorescence can be monitored with a fluorescence microplate reader. Digestion products from the elastin substrate have absorption maxima at ~505 nm and fluorescence emission maxima at ~515 nm. The peptide, N-methoxysuccinyl-Ala-Ala-Pro-Val-chloromethyl ketone, can be used as a selective, collective inhibitor of elastase when utilizing the EnzChek Elastase Assay Kit for screening for elastase inhibitors.

Collagen Stimulation Assay: Collagens (types I, II, III, IV and V) are synthesized as precursor molecules called procollagens. These precursor molecules contain additional peptide sequences, usually called "propeptides", at both the amino-terminal and the carboxy-terminal ends. During cellular expression and secretion, procollagens are assembled in the trimeric form and then cleaved at specific N- and C-terminal sites by specific endopeptidases, generating three fragments: procollagen-1 N-terminal propeptide (PINP), Type I collagen, and procollagen-1 carboxy-terminal propeptide (PICP).

The function of the propeptides is to facilitate the winding of procollagen molecules into a triple-helical conformation within the endoplasmic reticulum. The propeptides are cleaved off from the collagen triple helix molecule during its secretion, after which the triple helix collagens polymerize into extracellular collagen fibrils. Thus, the amount of the free propeptides reflects stoichiometrically the amount of collagen molecules synthesized (a relationship analogous to that between the carboxy-terminal peptide of proinsulin and the endogenously produced insulin). Collagen is an extracellular matrix protein critical for skin structure. Increased synthesis of collagen helps improve skin firmness and elasticity.

Quantitative detection of PICP in fibroblast cell extracts and culture supernatants may be performed with an enzyme immunoassay kit (e.g., Takara #MK101) to assess the effects of each of the active ingredients, any one of the combination of ingredients, or compositions having said combinations disclosed in the specification on the synthesis of PICP in skin. This bioassay may be used to examine effects on the production of procollagen peptide (a precursor to collagen) by human epidermal fibroblasts. The endpoint of this assay is a spectrophotometric measurement that reflects the presence of procollagen peptide and cellular viability. The assay employs the quantitative sandwich enzyme immunoassay technique whereby a monoclonal antibody specific for procollagen peptide is pre-coated onto a microplate. Standards and samples are pipetted into the wells and any procollagen peptide present is bound by the immobilized antibody. After washing away any unbound substances, an enzyme-linked polyclonal antibody specific for procollagen peptide is added to the wells. Following a wash to remove any unbound antibody-enzyme reagent, a substrate solution is added to the wells and color is developed in proportion to the amount of procollagen peptide bound in the initial step. Color development is stopped and the intensity of the color at 450 nm is measured using a microplate reader.

For generation of samples and controls, subconfluent normal human adult epidermal fibroblasts (Cascade Biologics) are cultivated in standard DMEM growth medium with 10% fetal bovine serum (Mediatech) at 37° C. in 10% $CO_2$. The cells are treated with each of the active ingredients, any one of the combination of ingredients, or compositions having said combinations disclosed in the specification and controls for 3 days. Following incubation, cell culture medium is collected and the amount of Type I procollagen peptide secretion is quantified using the sandwich enzyme linked immuno-sorbant assay (ELISA) from Takara (#MK101) as explained above.

Lysyl Oxidase Assay: A lysyl oxidase assay may be performed on skin cells (e.g., epidermal keratinocytes, fibroblasts, and/or dermal endothelial cells) to determine the ability of each of the active ingredients, any one of the combination of ingredients, or compositions having said combinations disclosed in the specification to stimulate expression of lysyl oxidase in skin. Lysyl oxidase can catalyze crosslinking of elastin and collagens, thereby providing for a more structurally rigid matrix for skin. By increasing expression of lysyl oxidase, increased crosslinking of elastin and collagens can occur, which can be beneficial in reducing the appearance of fine lines, wrinkles, sagging skin, and/or non-elastic skin.

B16 Pigmentation Assay: Melanogenesis is the process by which melanocytes produce melanin, a naturally produced pigment that imparts color to skin, hair, and eyes. Inhibiting melanogenesis is beneficial to prevent skin darkening and lighten dark spots associated with aging. This bioassay utilizes B16-F1 melanocytes (ATCC), an immortalized mouse melanoma cell line, to analyze the effect of each of the active ingredients, any one of the combination of ingredients, or compositions having said combinations disclosed in the specification on melanogenesis. The endpoint of this assay is a spectrophotometric measurement of melanin production and cellular viability. B16-F1 melanocytes, can be cultivated in standard DMEM growth medium with 10% fetal bovine serum (Mediatech) at 37° C. in 10% $CO_2$ and then treated with any one of the active ingredients, combination of ingredients, or compositions having said combinations disclosed in the specification for 6 days. Following incubation, melanin secretion is measured by absorbance at 405 nm and cellular viability is quantified.

Elastin Stimulation Assay: Elastin is a connective tissue protein that helps skin resume shape after stretching or contracting. Elastin is also an important load-bearing protein used in places where mechanical energy is required to be stored. Elastin is made by linking many soluble tropoelastin protein molecules, in a reaction catalyzed by lysyl oxidase. Elastin secretion and elastin fibers may be monitored in cultured human fibroblasts by staining of cultured human fibroblasts using immunofluorescent antibodies directed against elastin by a direct ELISA sandwich method. A Meso Scale Discovery system SECTOR 2400 Imaging system is used to analyze the results. Changes in elastin secretion and elastin fibers caused by each of the active ingredients, any one of the combination of ingredients, or compositions having said combinations disclosed in the specification may be determined by incubating cultured human fibroblasts with the active ingredient for a period of time before probing the cells or a lysate thereof with antibodies directed against elastin.

Oil Control Assay: An assay to measure reduction of sebum secretion from sebaceous glands and/or reduction of sebum production from sebaceous glands can be assayed by using standard techniques known to those having ordinary skill in the art. In one instance, the forehead can be used. Each of the active ingredients, any one of the combination of ingredients, or compositions having said combinations disclosed in the specification can be applied to one portion of the forehead once or twice daily for a set period of days (e.g., 1, 2, 3, 4, 5, 6, 7, 8, 9, 10, 11, 12, 13, 14, or more days), while another portion of the forehead is not treated with the composition. After the set period of days expires, then sebum secretion can be assayed by application of fine blotting paper to the treated and untreated forehead skin. This is done by first removing any sebum from the treated and untreated areas with moist and dry cloths. Blotting paper can then be applied to the treated and untreated areas of the forehead, and an elastic band can be placed around the forehead to gently press the blotting paper onto the skin. After 2 hours the blotting papers can be removed, allowed to dry and then transilluminated. Darker blotting paper correlates with more sebum secretion (or lighter blotting paper correlates with reduced sebum secretion.

Erythema Assay: An assay to measure the reduction of skin redness can be evaluated using a Minolta Chromometer. Skin erythema may be induced by applying a 0.2% solution of sodium dodecyl sulfate on the forearm of a subject. The area is protected by an occlusive patch for 24 hrs. After 24 hrs, the patch is removed and the irritation-induced redness can be assessed using the a* values of the Minolta Chroma Meter. The a* value measures changes in skin color in the red region. Immediately after reading, the area is treated with the active ingredients, any one of the combination of ingredients, or compositions having said combinations disclosed in the specification. Repeat measurements can be taken at regular intervals to determine the formula's ability to reduce redness and irritation.

Skin Clarity and Reduction in Freckles and Age Spots Assay: Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether each of the active ingredients, any one of the combination of ingredients, or compositions having said combinations disclosed in the specification is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$.

Skin Dryness, Surface Fine Lines, Skin Smoothness, and Skin Tone Assay: Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical Grading of Skin Tone Assay: Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical Grading of Skin Smoothness Assay: Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin Smoothness and Wrinkle Reduction Assay With Methods Disclosed in Packman et al. (1978): Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Appearance of Lines and Wrinkles Assay with Replicas: The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and are of the replicas covered by wrinkles or fine lines was determined.

Skin Firmness Assay with a Hargens Ballistometer: Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin Softness/Suppleness Assay with a Gas Bearing Electrodynamometer: Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

Surface Contour of the Skin Assay with a Profilometer/ Stylus Method: The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height (x-axis).

MELANODERM™ Assay: In other non-limiting aspects, the efficacy of each of the active ingredients, any one of the combination of ingredients, or compositions having said combinations disclosed in the specification can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing each of the active ingredients, any one of the combination of ingredients, or compositions having said combinations disclosed in the specification or with the base alone as a control. Alternatively, an untreated sample of the skin analog can be used as a control.

Production of Filaggrin: Changes in the production of filaggrin in keratinocytes due to each of the active ingredients, any one of the combination of ingredients, or compositions having said combinations disclosed in the specification can be measured. Filaggrin is the precursor to Natural Moisturizing Factor (NMF) in the skin. Increased NMF increases the moisture content of the skin. Filaggrin production in treated and non-treated keratinocytes can be determined using a bioassay that analyzes filaggrin concentration in keratinocyte cell lysates. A non-limiting example of a bioassay that can be used to quantify filaggrin production is the PROTEINSIMPLE® SIMON™ western blotting protocol. For each sample, normal human epidermal keratinocytes (NHEK) are grown in EPI-200-Mattek EPILIFE™ growth media with calcium from Life Technologies (M-EP-500-CA). NHEK are incubated in growth medium overnight at 37° C. in 5% $CO_2$ prior to treatment. NHEK are then incubated in growth medium with 1% test compound/extract or no compound/extract (negative control) for 24 to 36 hours. The NHEK can then be washed, collected, and stored on ice or colder until lysed on ice using a lysis buffer and sonication. The protein concentrations of the samples can be determined and used to normalize the samples. The lysates can be stored at −80° C. until use in the quantification assay.

The PROTEINSIMPLE® SIMON™ western blotting bioassay assay employs a quantitative western blotting immunoassay technique using an antibody specific for filaggrin to quantitatively detect filaggrin in the test samples. Cell samples are lysed and normalized for protein concentration. Normalized samples and molecular weight standards can then be loaded and ran on a denatured protein separation gel using capillary electrophoresis. The proteins in the gel are immobilized and immunoprobed using a primary antibody specific for filaggrin. The immobilized proteins can then be immunoprobed with an enzyme-linked detection antibody that binds the primary antibody. A chemiluminescent substrate solution can then be added to the immobilized proteins to allow chemiluminescent development in proportion to the amount of filaggrin bound in the immobilization. The chemiluminescent development is stopped at a specific time and the intensity of the chemiluminescent signal can be measured and compared to positive and negative controls.

Inhibition of Hyaluronidase Activity: Changes in the activity of hyaluronidase due to each of the active ingredients, any one of the combination of ingredients, or compositions having said combinations disclosed in the specification can be measured. Hyaluronidase is an enzyme that degrades HA. HA is a polysaccharide involved in stabilization of the structure of the matrix and is involved in providing turgor pressure to tissue and cells. As one non-limiting example, hyaluronidase activity can be determined using an in vitro protocol modified from Sigma-Aldrich protocol #EC 3.2.1.35. Briefly, hyaluronidase type 1-S from Sigma-Aldrich (H3506) is added to microplate reaction wells containing test compound or controls. Tannic acid can be used as a positive control inhibitor, no test compound can be added for the control enzyme, and wells with test compound or positive control but without hyaluronidase can be used as a background negative control. The wells are incubated at 37° C. for 10 minutes before addition of substrate (HA). Substrate is added and the reactions incubated at 37° C. for 45 minutes. A portion of each reaction solution is then transferred to and gently mixed in a solution of sodium acetate and acetic acid pH 3.75 to stop that portion of the reaction (stopped wells). The stopped wells and the reaction wells should both contain the same volume of solution after addition of the portion of the reaction solution to the stopped wells. Both the reaction wells and the stopped wells are incubated for 10 minutes at room temperature. Absorbance at 600 nm is then measured for both the reaction wells and the stopped wells. Inhibition can be calculated using the following formulas: Inhibitor (or control) activity=(Inhibitor stopped wells absorbance at 600 nm−inhibitor reaction wells absorbance at 600 nm); Initial activity=control enzyme absorbance at 600 nm; Percent Inhibition=[(Initial activity/Inhibitor Activity)*100]−100.

Peroxisome Proliferator-Activated Receptor Gamma (PPAR-γ) Activity: Changes in the activity of PPAR-γ due to each of the active ingredients, any one of the combination of ingredients, or compositions having said combinations disclosed in the specification can be measured. PPAR-γ is a receptor critical for the production of sebum. As one non-limiting example, the activity of PPAR-γ can be determined using a bioassay that analyzes the ability of a test compound or composition to inhibit binding of a ligand. Briefly, fluorescent small-molecule pan-PPAR ligand, FLUORMONE™ Pan-PPAR Green, available from Life Technologies (PV4894), can be used to determine if test compounds or compositions are able to inhibit binding of the ligand to PPAR-γ. The samples wells include PPAR-γ and fluorescent ligand and either: test compound or composition (test); a reference inhibitor, rosiglitazone (positive control); or no test compound (negative control). The wells are incubated for a set period of time to allow the ligand opportunity to bind the PPAR-γ. The fluorescence polarization of each sample well can then be measured and compared to the negative control well to determine the percentage of inhibition by the test compound or composition.

Cytokine array: Human epidermal keratinocytes are cultured to 70-80% confluency. The media in the plate is aspirated and 0.025% trypsin/EDTA is added. When the cells became rounded, the culture dish is gently tapped to release the cells. The trypsin/EDTA containing cells are removed from the culture dish and neutralized. Cells are centrifuged for 5 min. at 180×g to form a pellet of cells. The supernatant is aspirated. The resulting pellet is resuspended in EPILIFE™ media (Cascade Biologics). The cells are seeded in 6-well plates at approximately 10-20% confluency. After the cells became approximately 80% confluent, the media is aspirated and 1.0 ml of EPILIFE™, along with phorbol 13-Myristate 12-acetate ("PMA") (a known inducer of inflammation) and the test composition dilutions are added to two replicate wells (i.e., 1.0% (100 µl of 100× stock) and 0.1% (10 µl of 100× stock) test compositions are diluted into a final volume of 1 ml EpiLife Growth Medium). The media is gently swirled to ensure adequate mixing. In addition, 1.0 ml of EPILIFE™ is added to the control wells, with and without additional PMA. The plates are then incubated at 37±1° C. and 5.0±1% $CO_2$ for approximately 5 hours after dosing. Following this 5-hour incubation, all media is collected in conical tubes and frozen at −70° C.

For analysis, a 16-pad hybridization chamber is attached to 16-pad FAST slides arrayed in triplicate with 16 anti-cytokine antibodies plus experimental controls (Whatman BioSciences), and the slides are placed into a FASTFrame (4 slides per frame) for processing. Arrays are blocked for 15 min. at room temp. using 70 ml S&S Protein Array Blocking buffer (Whatman Schleicher and Scheull). Blocking buffer is removed and 70 ml of each supernatant sample is added to each array. Arrays are incubated for 3 hours at room temp. with gentle agitation. Arrays are washed 3 times with TBS-T. Arrays are treated with 70 ml of an antibody cocktail, containing one biotinylated antibody corresponding to each of the arrayed capture antibodies. Arrays are incubated for 1 hour at room temp. with gentle agitation. Arrays are washed 3 times with TBS-T. Arrays are incubated with 70 ml of a solution containing streptavidin-Cy5 conjugate for 1 hour at room temp. with gentle agitation. Arrays are washed 3 times with TBS-T, quickly rinsed in de-ionized water, and dried.

Slides can be imaged in a Perkin-Elmer ScanArray 4000 confocal fluorescent imaging system. Array images can be saved and analyzed using Imaging Research ArrayVision software. Briefly, spot intensities are determined by subtracting background signal. Spot replicates from each sample condition can be averaged and then compared to the appropriate controls.

Endothelial Tube Formation: Endothelial tube formation is involved in angiogenesis and micro-vessel capillary formation. Capillary formation and angiogenesis may contribute to redness and rosacea of the skin. The ability for endothelial cells to form tubes in the presence or absence of test extracts and compounds may be determined using a capillary tubule disruption assay with pre-formed primary human umbilical vein endothelial cells (HUVEC) in a cell culture system.

Briefly, HUVECs are cultured in vitro on Extracellular Matrix, which stimulates the attachment and tubular morphogenesis of endothelial cells to form capillary-like lumen structures. These in vitro formed capillary tubules are similar to human blood vessel capillaries in many aspects. The capillary tube assay is based on this phenomenon and is used for evaluation of potential vasculature targeting agents.

HUVEC cultures are grown in a 5% $CO_2$ 37° C. cell incubator. The full growth medium for HUVECs is Endothelial Cell Basal Medium (EBM) supplemented with 2% fetal bovine serum (FBS), 12 µg/ml bovine brain extract, 1 µg/ml hydrocortisone, and 1 µg/ml GA-1000 (gentamicin-amphothericin). HUVEC cultures between passage 3 and 8 may be used for all assay experiments.

HUVECs are pre-labeled with fluorescent agent Calcein AM and seeded in Extracellular Matrix coated 96-well culture plate with their full growth medium. After about four hours of the morphogenesis process, the endothelial capillary tubes should be formed. Then, test agent in designed doses in 50 µl volume is applied into the formed capillary tubule cultures as treatment conditions. The no-treatment controls can be added with vehicle of test agents. Sutent, a FDA approved anti-angiogenic drug one concentration can be included as assay performance control. After about six hours of treatment, the endothelial tubule morphology in each well is examined by microscopy, imaged, and the capillary disrupting activities under treatment conditions can be quantitatively analyzed. Each test conditions can be conducted in duplicate wells, including controls.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Cosmetic Ingredient Dictionary, Third Edition, CTFA, 1982
International Cosmetic Ingredient Dictionary, Fourth edition, CTFA, 1991
International Cosmetic Ingredient Dictionary and Handbook, Tenth Edition, CTFA, 2004
International Cosmetic Ingredient Dictionary and Handbook, Twelfth Edition, CTFA, 2008

The invention claimed is:

1. A method of increasing skin hydration, increasing ATP production in skin, increasing antioxidant capacity of skin, reducing glycation of skin, or a combination thereof, the method comprising topically applying to the skin a composition comprising an effective amount of *Chamomilla recutita* flower extract, *Vitis vinifera* seed extract, hydrolyzed sodium hyaluronate, Natural Moisturizing Factors (NMF), and optionally carnosine, wherein the NMF comprises sodium pyroglutamate, sodium lactate, arginine, aspartic acid, pyroglutamic acid, glycine, alanine, serine, valine, proline, threonine, isoleucine, histidine, and phenylalanine, and wherein topical application of the composition increases skin hydration, increases ATP production in skin, increases antioxidant capacity of skin, and/or reduces glycation of skin.

2. The method of claim 1, wherein the composition comprises 0.001 to 1% by weight of *Chamomilla recutita* flower extract, 0.001 to 0.1% by weight of *Vitis vinifera* seed extract, 0.001 to 0.1% by weight of hydrolyzed sodium hyaluronate, 0.001 to 1% by weight of Natural Moisturizing Factors, and 0.001 to 1% by weight of carnosine.

3. The method claim 1, wherein the composition further comprises one or more of: a humectant, an emollient, a skin protecting agent, and/or a pH adjuster.

4. The method of claim 1, wherein the composition further comprises: 1 to 95% by weight water; 1 to 15% by weight glycerin; and/or 0.01 to 1% by weight caprylyl glycol.

5. The method of claim 1, wherein the composition further comprises: 0.1 to 10% by weight dimethicone; 0.1 to 10% by weight propanediol; and/or 0.1 to 5% by weight betaine.

6. The method of claim 1, wherein the composition further comprises:
- 1 to 10% by weight cetearyl ethylhexanoate;
- 1 to 10% by weight pentylene glycol;
- 0.1 to 10% by weight dimethicone;
- 0.1 to 5% by weight cyclopentasiloxane;
- 0.01 to 3% by weight PEG-12 dimethicone; and/or
- 0.01 to 1% by weight dimethiconol.

7. The method of claim 1, wherein the composition further comprises: 0.001 to 1% by weight 1,2-hexanediol.

8. The method of claim 1, wherein the composition further comprises:
- 0.1 to 10% by weight dimethicone;
- 0.1 to 10% by weight caprylic/capric triglyceride;
- 0.1 to 10% by weight squalene;
- 0.1 to 10% by weight butylene glycol;
- 0.1 to 5% by weight cyclopentasiloxane;
- 0.1 to 5% by weight *Prunus armeniaca* kernel oil;
- 0.1 to 5% by weight dipropylene glycol;
- 0.01 to 3% by weight PCA dimethicone;
- 0.1 to 3% by weight betaine; and/or
- 0.1 to 1% by weight hydrogenated lecithin.

9. The method of claim 1, wherein the composition comprises an effective amount of *Vitis vinifera* (Grape) seed extract to increase ATP production in skin by at least 10% after topical application of the composition to the skin.

10. The method of claim 1, wherein the composition comprises an effective amount of *Chamomilla recutita* flower extract and carnosine to reduce glycation of skin by at least 50% after topical application of the composition to the skin.

* * * * *

UNITED STATES PATENT AND TRADEMARK OFFICE
CERTIFICATE OF CORRECTION

PATENT NO. : 11,696,888 B2  Page 1 of 1
APPLICATION NO. : 17/303288
DATED : July 11, 2023
INVENTOR(S) : Tiffany Carle et al.

It is certified that error appears in the above-identified patent and that said Letters Patent is hereby corrected as shown below:

In the Claims

In Claim 9, Column 42, Line 9, please delete "(Grape)" therefore.

Signed and Sealed this
Eighth Day of August, 2023

Katherine Kelly Vidal
*Director of the United States Patent and Trademark Office*